(12) United States Patent  (10) Patent No.: US 8,167,910 B2
Nilsson  (45) Date of Patent: May 1, 2012

(54) BONE SCREW AND ASSOCIATED ASSEMBLY AND METHODS OF USE THEREOF

(75) Inventor: Carl Michael Nilsson, Cleveland Heights, OH (US)

(73) Assignee: Innovative Delta Technology LLC, Cleveland Heights, OH (US)

( * ) Notice: Subject to any disclaimer, the term of this patent is extended or adjusted under 35 U.S.C. 154(b) by 797 days.

(21) Appl. No.: 11/549,800

(22) Filed: Oct. 16, 2006

(65) Prior Publication Data

US 2008/0161859 A1  Jul. 3, 2008

(51) Int. Cl.
*A61B 17/70* (2006.01)

(52) U.S. Cl. ........ 606/264; 606/265; 606/270; 606/300; 606/305

(58) Field of Classification Search .......... 606/264–279, 606/300–321, 60, 61
See application file for complete search history.

(56) References Cited

U.S. PATENT DOCUMENTS

| | | | |
|---|---|---|---|
| 5,207,678 A | 5/1993 | Harms et al. | |
| 5,360,431 A | 11/1994 | Puno et al. | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,496,321 A | 3/1996 | Puno et al. | |
| 5,536,268 A | 7/1996 | Griss | |
| 5,624,442 A | 4/1997 | Mellinger et al. | |
| 5,630,817 A * | 5/1997 | Rokegem et al. | 606/269 |
| 5,647,873 A | 7/1997 | Errico et al. | |
| 5,669,911 A | 9/1997 | Errico et al. | |
| 5,690,630 A | 11/1997 | Errico et al. | |
| 5,733,285 A | 3/1998 | Errico et al. | |
| 5,733,286 A | 3/1998 | Errico et al. | |
| 5,782,833 A | 7/1998 | Haider | |
| 5,797,911 A | 8/1998 | Sherman et al. | |
| 5,879,350 A | 3/1999 | Sherman et al. | |
| 5,885,286 A | 3/1999 | Sherman et al. | |
| 5,910,142 A | 6/1999 | Tatar | |
| 5,947,967 A | 9/1999 | Barker | |
| 5,964,760 A | 10/1999 | Richelsoph | |
| 6,053,917 A | 4/2000 | Sherman et al. | |
| 6,113,601 A | 9/2000 | Tatar | |
| 6,287,311 B1 | 9/2001 | Sherman et al. | |

(Continued)

OTHER PUBLICATIONS

Aesculap, Inc., S4 Spinal System, Sales literature, 2004, Aesculap, printed in U.S.A.

(Continued)

*Primary Examiner* — Eduardo C Robert
*Assistant Examiner* — Christina Negrelli
(74) *Attorney, Agent, or Firm* — Hahn Loeser & Parks LLP; John J. Cunniff

(57) ABSTRACT

A bone screw assembly comprises a bone screw having a shaft and a head, a stabilizer retainer, a set screw, and a housing having a proximal opening, biased to one side, and a distal opening that open on an interior cavity. The stabilizer retainer has a cylindrical channel that receives a stabilizer. The retainer has flexible portions that allow passage of the stabilizer into the channel. An arcuate wall of the channel maintains contact with the stabilizer within the channel. The housing is adapted to receive the bone screw, the stabilizer retainer and the set screw in the interior cavity. The housing has a channel that permits passage of the stabilizer though the housing. The set screw is engaged in the distal opening. The set screw and stabilizer retainer engage and prevent movement of the flexible portions, preventing movement of the stabilizer from the stabilizer retainer.

22 Claims, 29 Drawing Sheets

U.S. PATENT DOCUMENTS

| | | |
|---|---|---|
| 6,402,749 B1 | 6/2002 | Ashman |
| 6,485,494 B1 | 11/2002 | Haider |
| 6,540,748 B2 | 4/2003 | Lombardo |
| 6,565,567 B1 | 5/2003 | Haider |
| 6,626,908 B2 | 9/2003 | Cooper et al. |
| 6,709,434 B1 | 3/2004 | Gournay et al. |
| 6,716,214 B1 | 4/2004 | Jackson |
| 6,733,502 B2 | 5/2004 | Altarac et al. |
| 6,740,086 B2 | 5/2004 | Richelsoph |
| 6,755,830 B2 * | 6/2004 | Minfelde et al. .............. 606/278 |
| 6,869,433 B2 | 3/2005 | Glascott |
| 6,974,460 B2 | 12/2005 | Carbone et al. |
| 7,007,699 B2 | 3/2006 | Martinelli et al. |
| RE39,089 E | 5/2006 | Ralph et al. |
| 7,186,255 B2 * | 3/2007 | Baynham et al. ............. 606/266 |
| 7,270,665 B2 | 9/2007 | Morrison et al. |
| 7,291,151 B2 | 11/2007 | Alvarez |
| 7,377,923 B2 | 5/2008 | Purcell et al. |
| 7,524,326 B2 * | 4/2009 | Dierks ........................... 606/308 |
| 7,803,174 B2 * | 9/2010 | Denis et al. .................... 606/250 |
| 2001/0023350 A1 | 9/2001 | Chio |
| 2002/0010467 A1 | 1/2002 | Cooper et al. |
| 2002/0035366 A1 | 3/2002 | Walder et al. |
| 2002/0151900 A1 | 10/2002 | Glascott |
| 2003/0032957 A1 | 2/2003 | McKinley |
| 2003/0125741 A1 * | 7/2003 | Biedermann et al. ........... 606/61 |
| 2003/0199873 A1 | 10/2003 | Richelsoph |
| 2004/0097933 A1 | 5/2004 | Lourdel et al. |
| 2004/0158247 A1 | 8/2004 | Sitiso et al. |
| 2004/0193160 A1 | 9/2004 | Richelsoph |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0038430 A1 | 2/2005 | McKinley |
| 2005/0049588 A1 | 3/2005 | Jackson |
| 2005/0055026 A1 | 3/2005 | Biedermann |
| 2005/0080415 A1 | 4/2005 | Keyer et al. |
| 2005/0154391 A1 * | 7/2005 | Doherty et al. ................. 606/61 |
| 2005/0187548 A1 | 8/2005 | Butler et al. |
| 2005/0192571 A1 | 9/2005 | Abdelgany |
| 2005/0192572 A1 | 9/2005 | Abdelgany |
| 2005/0192573 A1 | 9/2005 | Abdelgany |
| 2005/0261687 A1 | 11/2005 | Garamszegi |
| 2006/0025771 A1 * | 2/2006 | Jackson ........................... 606/61 |
| 2006/0036242 A1 | 2/2006 | Nilsson et al. |
| 2006/0036244 A1 | 2/2006 | Spitler et al. |
| 2006/0036252 A1 | 2/2006 | Baynham et al. |
| 2006/0058788 A1 | 3/2006 | Hammer et al. |
| 2006/0058880 A1 | 3/2006 | Wysocki et al. |
| 2006/0084996 A1 | 4/2006 | Metz-Stavenhagen |
| 2006/0100622 A1 | 5/2006 | Jackson |
| 2006/0149241 A1 | 7/2006 | Richelsoph |
| 2006/0149372 A1 | 7/2006 | Paxson et al. |
| 2006/0155278 A1 | 7/2006 | Warnick |
| 2006/0235389 A1 * | 10/2006 | Albert et al. .................... 606/61 |
| 2006/0293659 A1 | 12/2006 | Alvarez |
| 2007/0288004 A1 | 12/2007 | Alvarez |
| 2008/0015586 A1 | 1/2008 | Krishna et al. |
| 2008/0021473 A1 | 1/2008 | Butler et al. |
| 2009/0163961 A1 * | 6/2009 | Kirschman .................... 606/301 |

OTHER PUBLICATIONS

Surgical Dynamics, Inc., Spiral Radius 90D, Sales literature, 2001, Surgical Dynamics, Inc., printed in U.S.A.

* cited by examiner

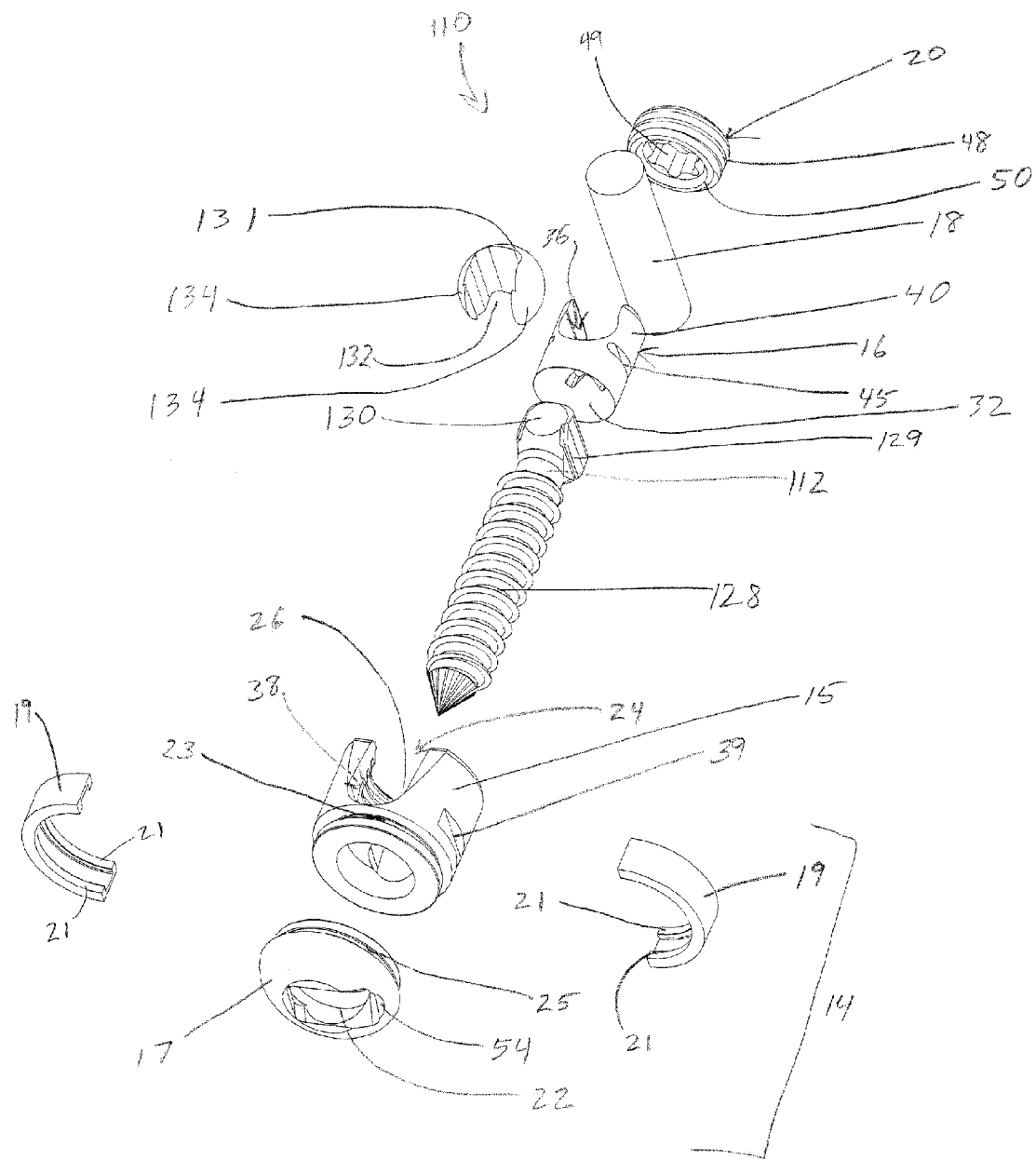

BONE SCREW AND ASSOCIATED ASSEMBLY AND METHODS OF USE THEREOF

BACKGROUND OF THE INVENTION

This invention relates to fixation devices for the spinal column. More particularly, this invention relates to a bone screw and associated components that may also be referred to as a pedicle screw assembly.

The spine is formed of a series of bones called vertebrae. There are 33 vertebrae, which are grouped as cervical, thoracic, lumbar, sacral, and coccygeal vertebrae, according to the regions of the spine they occupy. A typical vertebra consists of two essential parts, an anterior segment or body, and a posterior part, or vertebral or neural arch. These two parts enclose a foramen, the vertebral foramen. Together, the vertebral foramen of the vertebrae form a canal for the protection of the spinal cord. The vertebral arch consists of a pair of pedicles and a pair of laminae.

The body is the largest part of a vertebra, and is more or less cylindrical in shape. Its upper and lower surfaces are flattened. In front, the body is convex from side to side and concave from above downward. Behind, it is flat from above downward and slightly concave from side to side. The pedicles are two short, thick processes, which project backward, one on either side, from the upper part of the body, at the junction of its posterior and lateral surfaces.

Over the years, various techniques and systems have been developed for correcting spinal injuries and/or degenerative spinal processes. Spinal correction frequently requires stabilizing a portion of the spine to facilitate fusing portions of the spine or other correction methodologies. Medical correction of this type is frequently employed for many spinal conditions, such as, for example, degenerative disc disease, scoliosis, spinal stenosis, or the like. Frequently, these corrections also require the use of implants, such as, bone grafts. Stabilizing the spine allows bone growth between vertebral bodies such that a portion of the spine is fused into a solitary unit.

Several techniques and systems have been developed for correcting and stabilizing the spine and facilitating fusion at various levels of the spine. In one type of system, a rod is disposed longitudinally along the length of the spine in the region of concern. The rod is arranged according to the anatomy and the correction desired. In this system, the rod is aligned along the spine and engages various vertebrae along its length. The rod engages, or more typically, a pair of parallel rods engage the spine using fixation elements, such as anchors, attached to vertebral bodies by a bone screw that is inserted into the pedicle and penetrates into the body of the vertebra.

Anatomy and correction frequently require aligning the rod and screw at various angles along the length of the portion of correction. In order to provide this alignment, polyaxial screws/anchors have been developed. Many variations of bone screw and rod fixation systems exist on the market today. However, prior systems have been limited in the amount of angulation permitted relative to the place of attachment to the spine. Additionally, prior systems have involved the securing of a screw assembly to a support rod by direct contact between a set screw and the rod. This contact causes subtle damage to the support rod caused by plastic deformation of the rod by the set screw.

Therefore, there is a need for a bone screw assembly that permits a wide range of angulation relative to the place of attachment to the spine and the support rod while providing an effective and secure lock of the screw and rod in the desired position.

There is also a need for a mechanism of attachment of a spinal stabilizer or support rod to a bone screw that minimizes the possibility of damage to the rod by a set screw securing the rod to the bone screw.

There is also the need for a bone screw adapted to allow for placement into the pedicle and subsequent attachment of a housing to the bone screw in minimally invasive surgery.

SUMMARY OF THE INVENTION

It is, therefore, an aspect of the present invention to provide a bone screw assembly that provides an increased amount of allowable angulation between a spinal stabilizer rod and the screw axis.

In addition, it is another aspect of the present invention to provide a bone screw assembly that provides a mechanism of attachment of a spinal stabilizer or support rod to a bone screw that minimizes the possibility of damage to the rod by a set screw securing the rod to the bone screw.

It is still another aspect of the present invention to provide a bone screw that may be placed prior to housing placement, thereby allowing the screw system to be used in minimally invasive surgery.

In general, one embodiment of the present invention provides a bone screw assembly comprising a bone screw having a shaft and a head assembly, a stabilizer retainer adapted to engage the head of the bone screw, a set screw adapted to contact the stabilizer retainer, and a housing having a proximal opening and a distal opening that open on an interior cavity. The stabilizer retainer is generally cylindrical in shape with a cylindrical channel therein adapted to receive a stabilizer. The stabilizer retainer has flexible portions that allow passage of the stabilizer into the channel. An arcuate wall of the channel is adapted to maintain contact with at least a majority of the stabilizer located within the channel. The housing has a proximal opening and a distal opening that open on an interior cavity. The housing is adapted to receive the bone screw, the stabilizer retainer and the set screw in the interior cavity. The housing has a channel adapted to permit the passage of the stabilizer through the housing, and the housing is adapted to secure the set screw in the distal opening. The set screw and stabilizer retainer are adapted to engage in such a way that movement of the flexible portions of the stabilizer retainer is prevented, thereby maintaining contact between the stabilizer and the wall of the stabilizer retainer channel such that movement of the stabilizer from the stabilizer retainer is prevented.

In another embodiment, a bone screw assembly comprises a bone screw containing a shaft, a head, and a circumferential rim adjacent to and extending outward from the shaft forming a first annular cavity between the rim and the head. In some examples, the head may take any number of configurations including a cylinder, an outwardly tapered cylinder, or configurations such as those having an eliptical or polygonal cross section. In one example, the head has a hexagonal cross section. The head may be adapted to receive and secure a bone screw cap by an interference fit where the bone screw cap comprises an interior cavity.

In other examples, the head may have a tapered cylindrical configuration or a bone screw cap may comprises one or more slots extending though the sides of the cap into the cavity. In other examples, the bone screw assembly additionally comprises a generally cylindrical housing with a single central axis and with a proximal opening and a distal opening accessing an interior cavity, and the interior cavity comprises two generally spherical, connected cavities that connect to each other along the central axis of housing. The housing also has a channel, which is approximately perpendicular to the central axis of the housing, and is adapted to permit a stabilizer to be positioned within and extend through the housing. The walls of the housing may additionally be chamfered to permit angulation of the stabilizer within the channel.

In still other examples, the bone screw assembly includes a generally cylindrical housing with a single central axis, and with a proximal opening and a distal opening accessing an interior cavity that is generally cylindrical and follows the central axis of the housing The bone screw assembly may also include a set screw adapted to engage the housing. The housing may have a channel approximately perpendicular to the central axis of the housing, creating two opposed arcuate sections in the housing, and a pair of tabs which extend essentially parallel to the arcuate sections, wherein the tabs have an upper section and a lower section, and wherein the upper sections are approximately half the width of the lower sections and are adapted to cooperate to essentially surround a stabilizer in use and are further adapted to contact the set screw, such that the rotational movement of the set screw deflects the tabs in such a way that the tabs engage the stabilizer. In still another example, the bone screw assembly additionally comprises a generally cylindrical housing with a single central axis and with a proximal opening accessing a lower, at least partially spherical cavity adapted to accommodate the bone screw and the bone screw cap when the bone screw is inserted through the proximal opening, and a distal opening accessing an upper, generally cylindrical cavity, and wherein the upper cavity is adapted to accommodate a stabilizer retainer, which is adapted to be inserted into the upper cavity through the distal opening. The housing may also have a first channel, which is approximately perpendicular to the central axis of the housing, and is adapted to permit a stabilizer to be positioned within and extend through the housing, and the side walls of the housing bordering the first channel may be chamfered. Further, the upper cavity and the lower cavity may communicate through a diaphragm member located between the upper cavity and the lower cavity.

The present invention also provides a bone screw assembly comprising a bone screw having a shaft with a central axis, and a head, wherein the head is biased to one side of the central axis of the shaft. The head may be biased between about 0.1 and about 3 mm from the central axis of the shaft and may also or alternatively have a slot adapted to engage a driver, wherein the slot is positioned generally at or near the center of the central axis. The bone screw assembly may also include a generally cylindrical housing, where the housing comprises a single central axis and with a proximal opening and a distal opening accessing a generally cylindrical interior cavity. The housing may also have a channel generally perpendicular to the central axis adapted to receive a stabilizer and creating two opposed arcuate sections in the housing. The housing may be further adapted to receive a set screw, and the proximal opening may biased relative to the central axis of the housing.

In some embodiments, the proximal opening may be selected from circular and non-circular openings that may be centered on or biased relative to the central axis of the housing. In other embodiments, the location of the proximal opening may be adjustable. For example, the housing may include an upper portion and a lower portion that are attachable to each other. The lower portion contains the proximal opening and may be oriented in different positions relative to the upper portion. The upper and lower portions are also attachable to each other. In this way, the location of a biased proximal opening may be located through 360 degrees around the axis of the housing. In one example, the upper and lower portions may have detent locking members that engage each other to provide an interference fit between the upper and lower portions of the housing. Alternatively, the upper and lower portions may be clamped together by one or more additional clamping members.

In the present invention, it is not necessary for there to be additional spaces or slots in the housing, other than the channel for passage of the stabilizer through the housing, to provide proper placement and securing of the stabilizer. Therefore, in certain embodiments, the housing includes walls adjacent to the housing channel that consist of two opposed, continuous, arcuate segments. Similarly, the present invention eliminates the need for additional spaces or slots in the stabilizer receiver to provide proper placement and securing of the stabilizer in the stabilizer retainer. Therefore, in certain embodiments, the stabilizer retainer includes walls adjacent to the stabilizer retainer channel that consist of two opposed, continuous, arcuate segments. These walls may also comprise the flexible portion of the stabilizer retainer.

The present invention also provides a bone screw comprising a shaft portion and a head assembly, wherein the head assembly comprises a head base, at least one tab located on a side of and projecting from the head base and a head clamp containing at least one detent locking member adapted to interact with the at least one tab to provide an interference fit between the head base and the head clamp. In certain embodiments, the head assembly comprises two tabs on opposite sides of the head and a head clamp comprising two detent locking members that engage the tabs. In certain other embodiments, the head assembly is approximately spherical when assembled. The bone screw may also be used in the bone screw assembly as described herein.

The present invention also provides a method treating a patient where the method includes attaching the bone screw assembly of the present invention to a bone of the patient. The design of the bone screw assembly of the present invention provides the advantage to a surgeon of providing a subtle tactile feedback of a positive lock of components when they are properly positioned. This includes a tactile feedback of the stabilizer locking into place in the stabilizer retainer and/ or of the head clamp locking into place on the head base.

BRIEF DESCRIPTION OF THE DRAWINGS

FIG. 4B is an exploded view of the embodiment shown in FIG. 4A from an alternate elevation:

DETAILED DESCRIPTION OF THE INVENTION

Figure 1A:
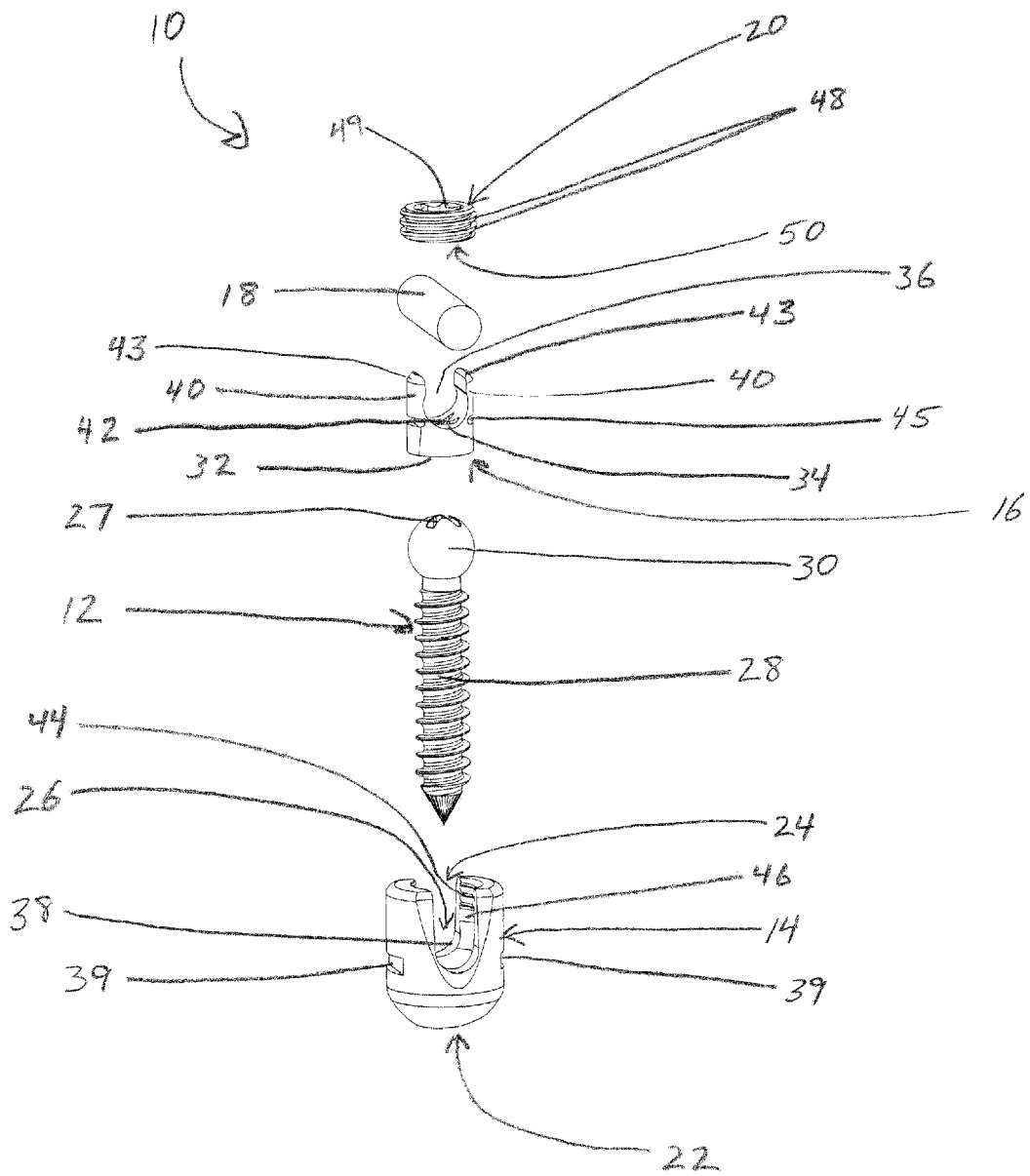
FIG. 1A is an exploded view of an embodiment of a bone screw assembly of the present invention.
Figure 1B:
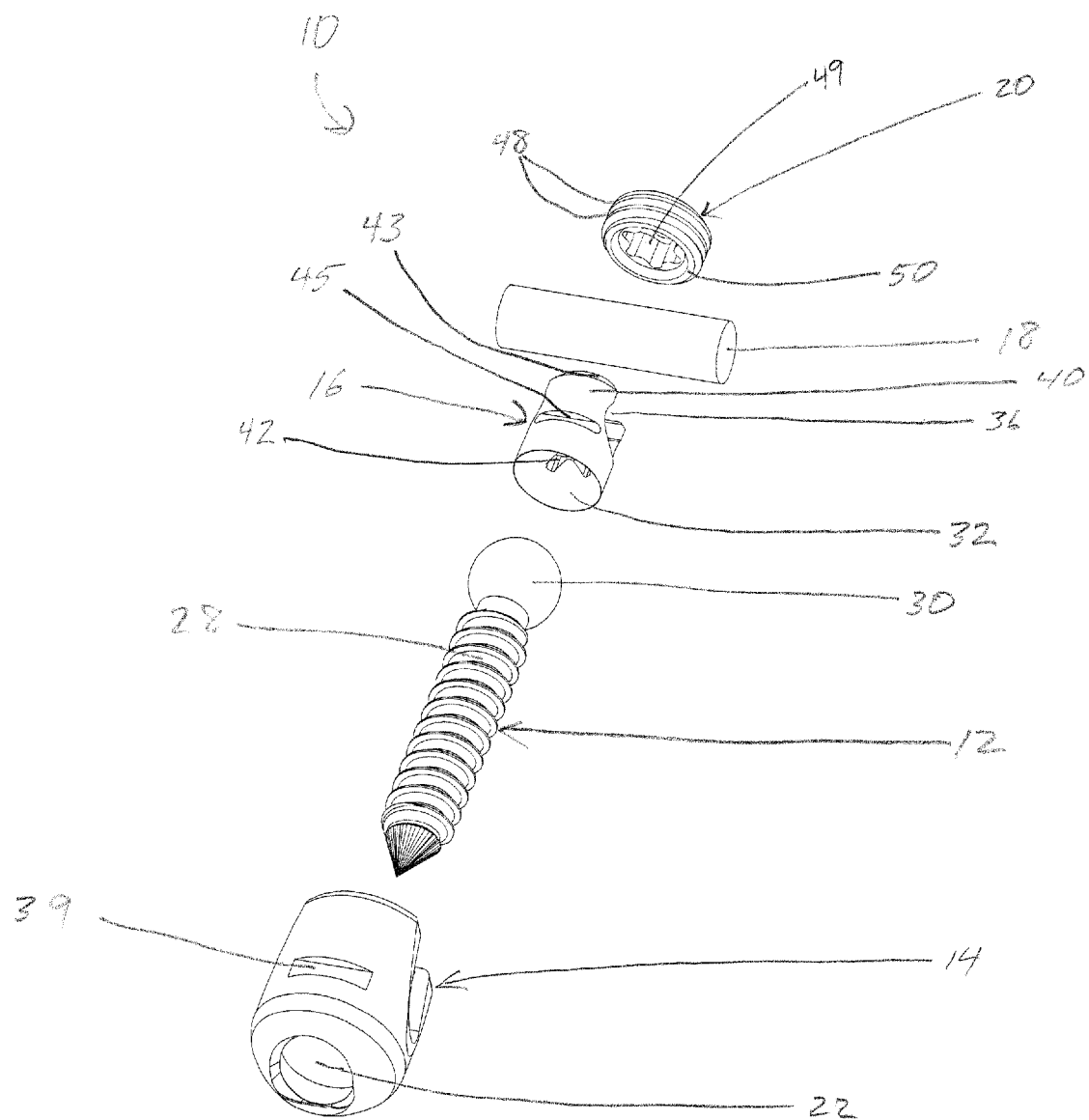
FIG. 1B is an exploded view of the embodiment shown in FIG. 1A from an alternate elevation.

The present invention is directed toward a bone screw and an associated assembly, especially for application in the spinal stabilization arena. The following examples should not be viewed as limiting the scope of the invention. The claims will serve to define the inventions. Additionally, it should be noted that elements of one example may be combined with elements of another example, except where the function of the components prohibits such combination. The following examples are non-limiting therefore in their arrangements and combinations of elements.

As shown in the Figures, a bone screw assembly 10 comprises a bone screw 12 and a housing 14. Bone screw 12 has two portions, a shaft 28 and a head 30. In the examples shown, housing 14 is generally cylindrical, with a single central axis, with a proximal opening 22 and a distal opening 24 accessing an interior cavity 26. Interior cavity 26 is generally cylindrical. However, the lower end of cavity 26 adjacent to proximal opening 22 has an interior wall that narrows inwardly to generally accommodate the shape of head 30 when bone screw 12 protrudes from proximal opening 22. The upper end of cavity 26, adjacent to distal opening 24 may be threaded with threads 44 to accommodate set screw 20. Adjacent to threads 44 are inset areas 46 which accommodate tabs 40 of insert 16 as described more fully below. Housing 14 may additionally have outer grooves 39 which provide a location for placement and grasping of the housing 14 by an insertion instrument (not shown). In one particular embodiment, the outer surface of housing 14 is devoid of threads on its upper end adjacent to distal opening 24 and presents a smooth, uninterrupted surface between grooves 39 and edge of the housing adjacent to distal opening 24. Housing 14 also has a channel 38 which allows positioning of a stabilizer or rod 18 through housing 14.

Figure 2:
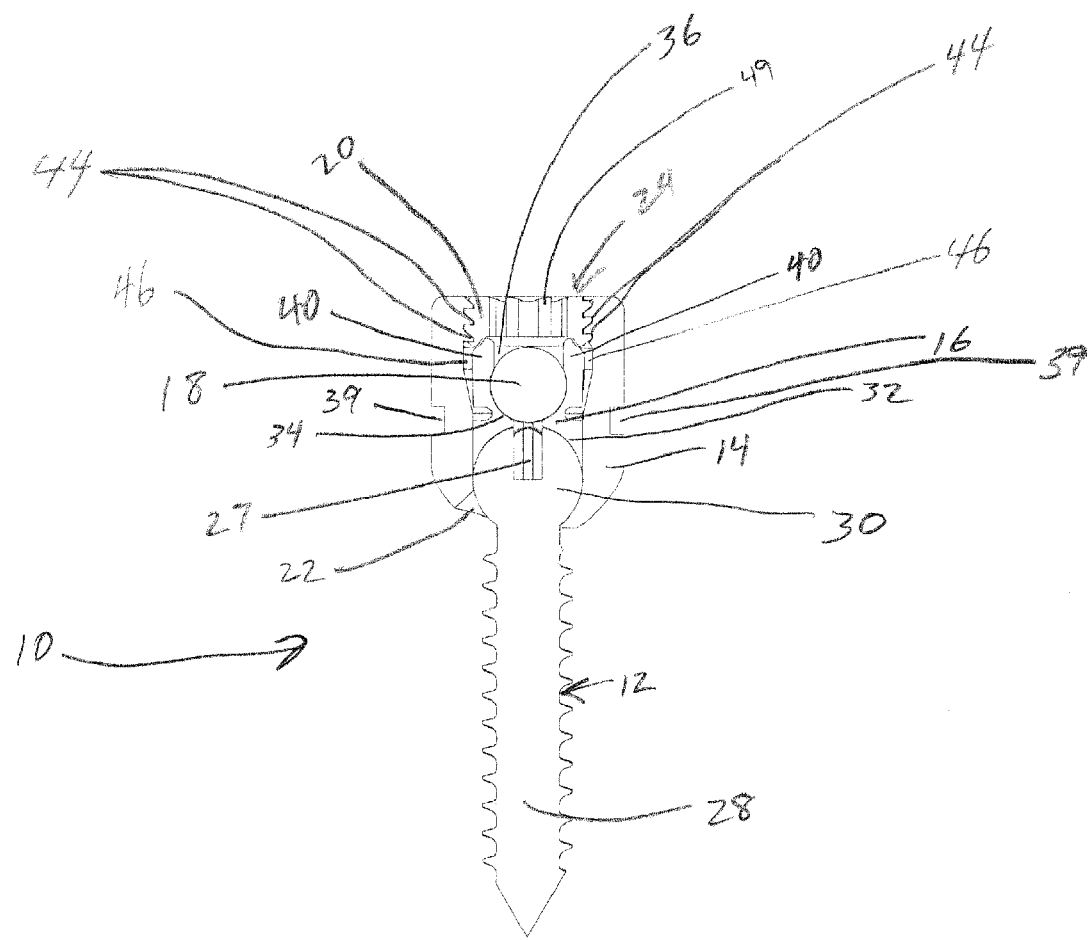
FIG. 2 is a cross sectional view of the embodiment of FIG. 1, as assembled.
Figure 3A:
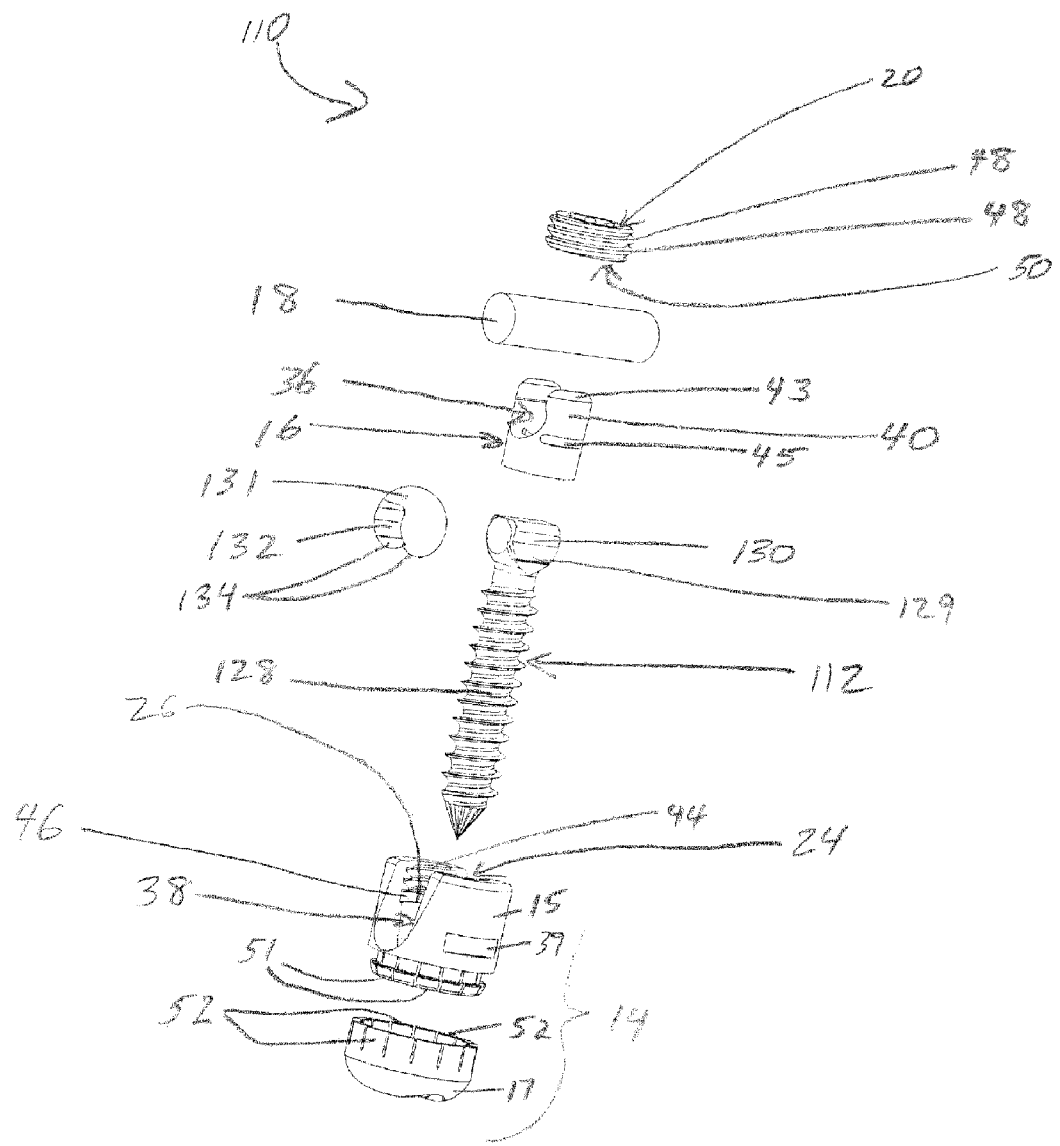
FIG. 3A is an exploded view of another embodiment of the bone screw assembly of the present invention.
Figure 3B:
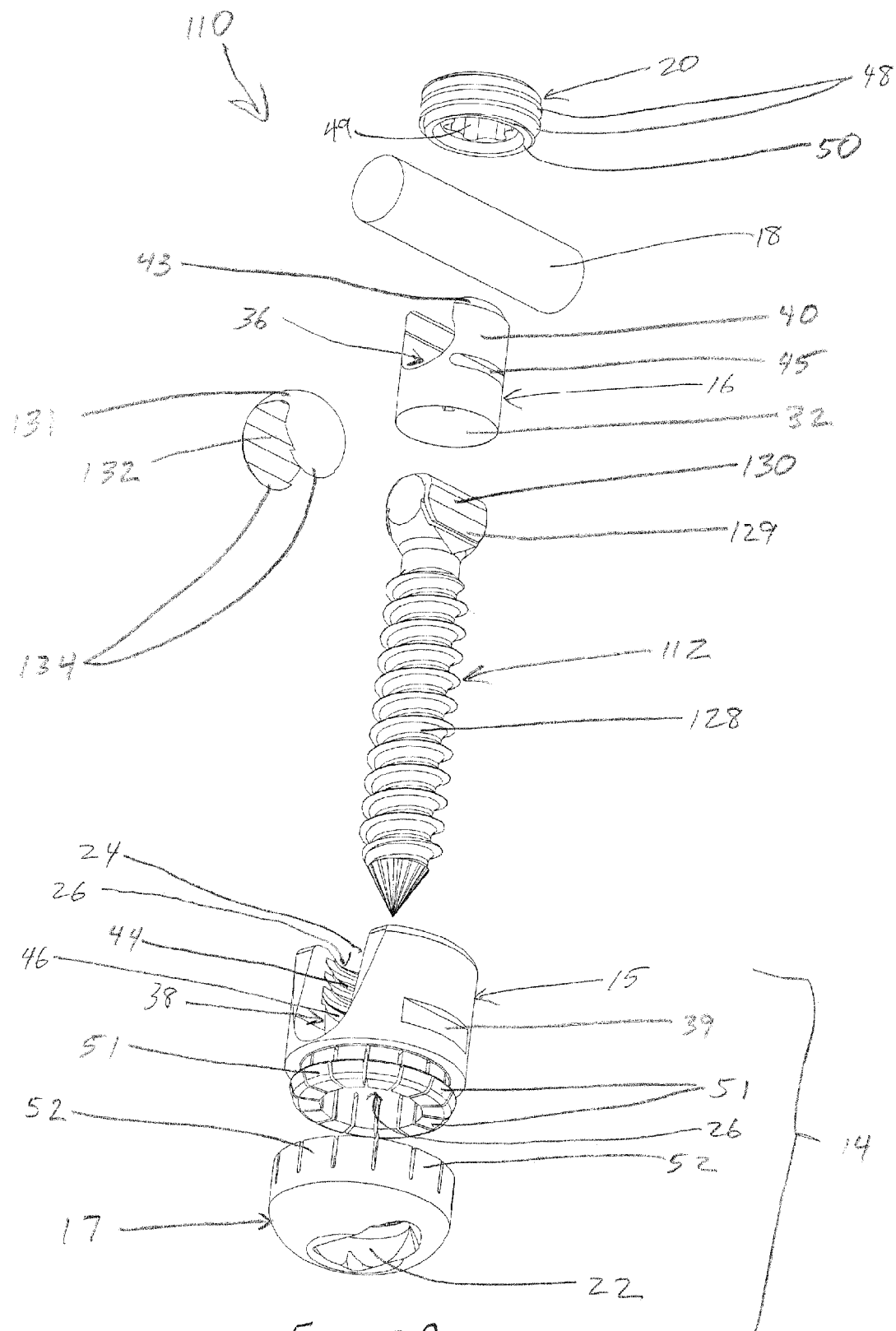
FIG. 3B is an exploded view of the embodiment shown in FIG. 3A from an alternate elevation.
Figure 3C:
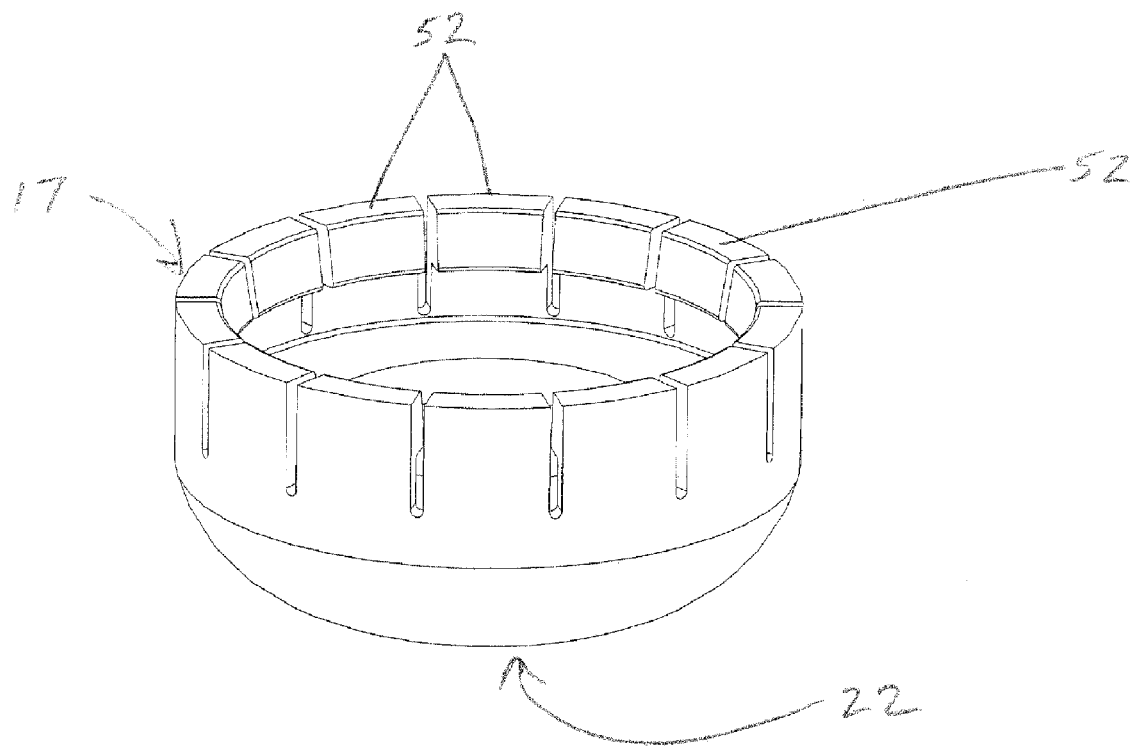
FIG. 3C is a side view of the lower portion of the housing shown in FIGS. 3A and 3B.
Figure 3D:
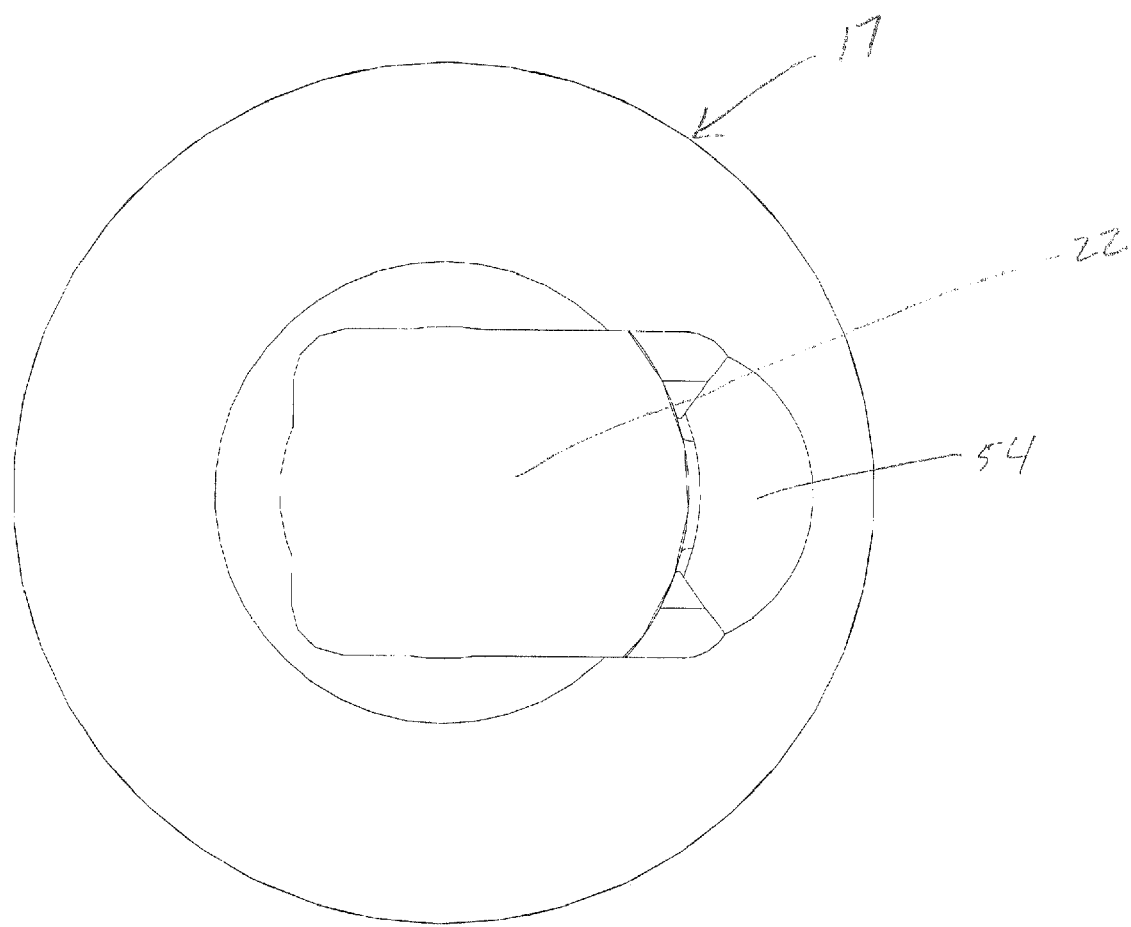
FIG. 3D is a lower view of the lower portion of the housing shown in FIGS. 3A and 3B.
Figure 3E:
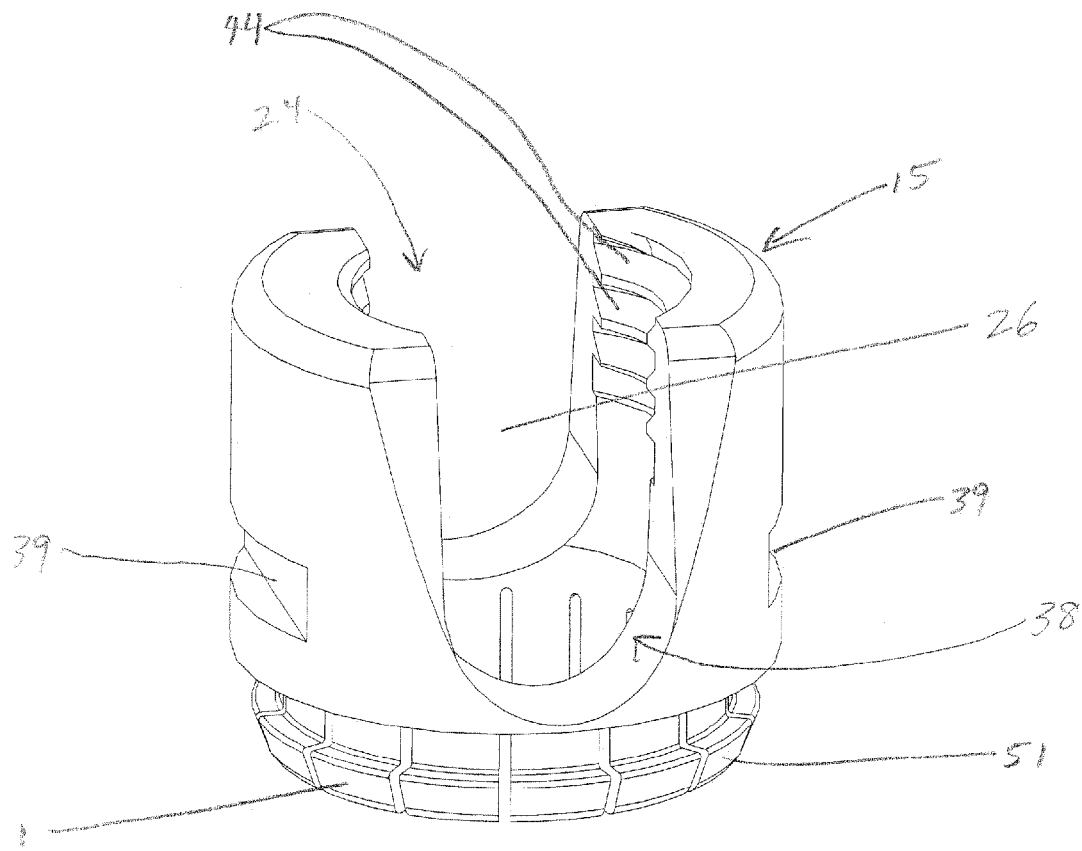
FIG. 3E is a side view of the upper portion of the housing shown in FIGS. 3A and 3B.
Figure 4A:
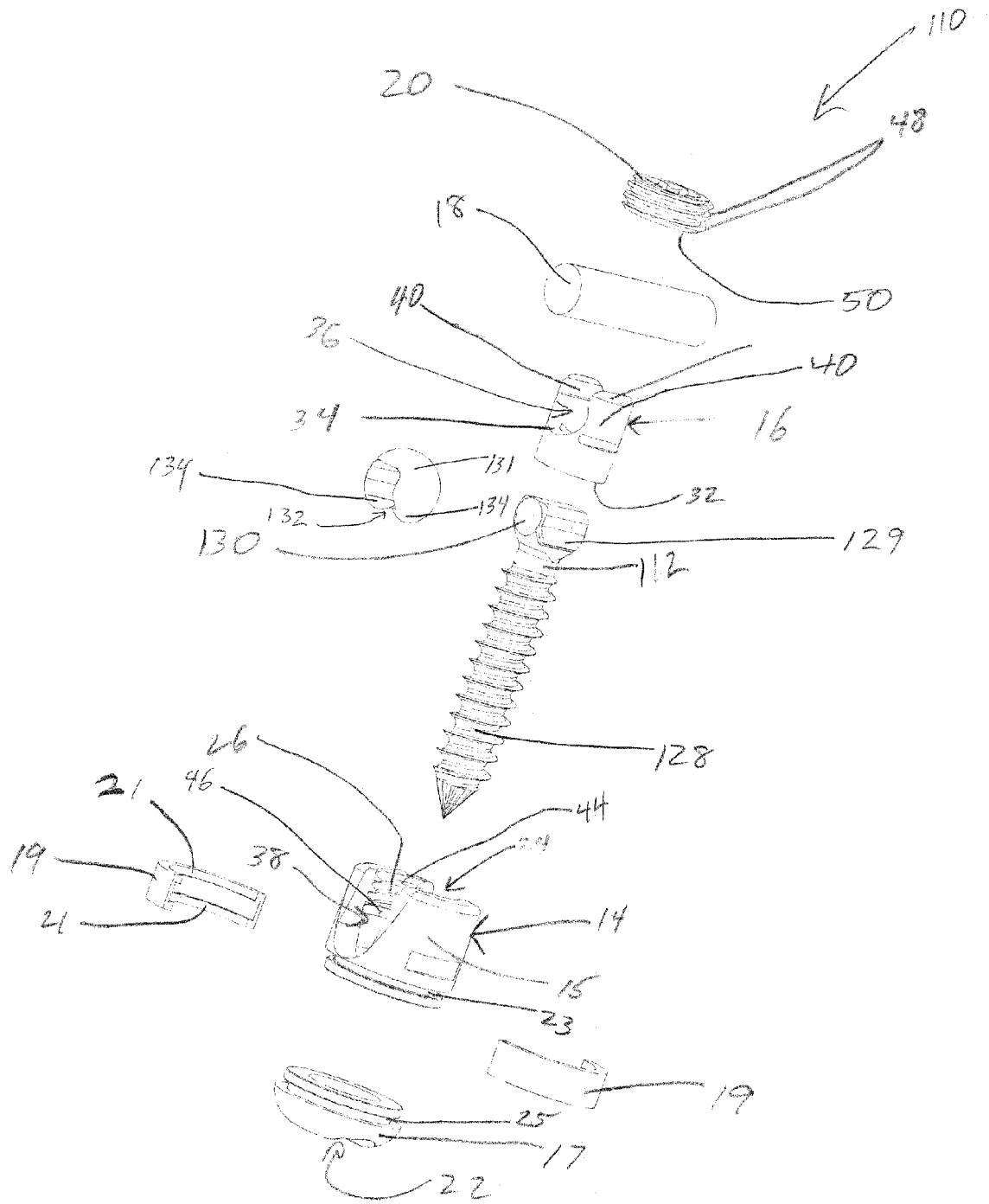
FIG. 4A is an exploded view of another embodiment of the bone screw assembly of the present invention.
Figure 4C:
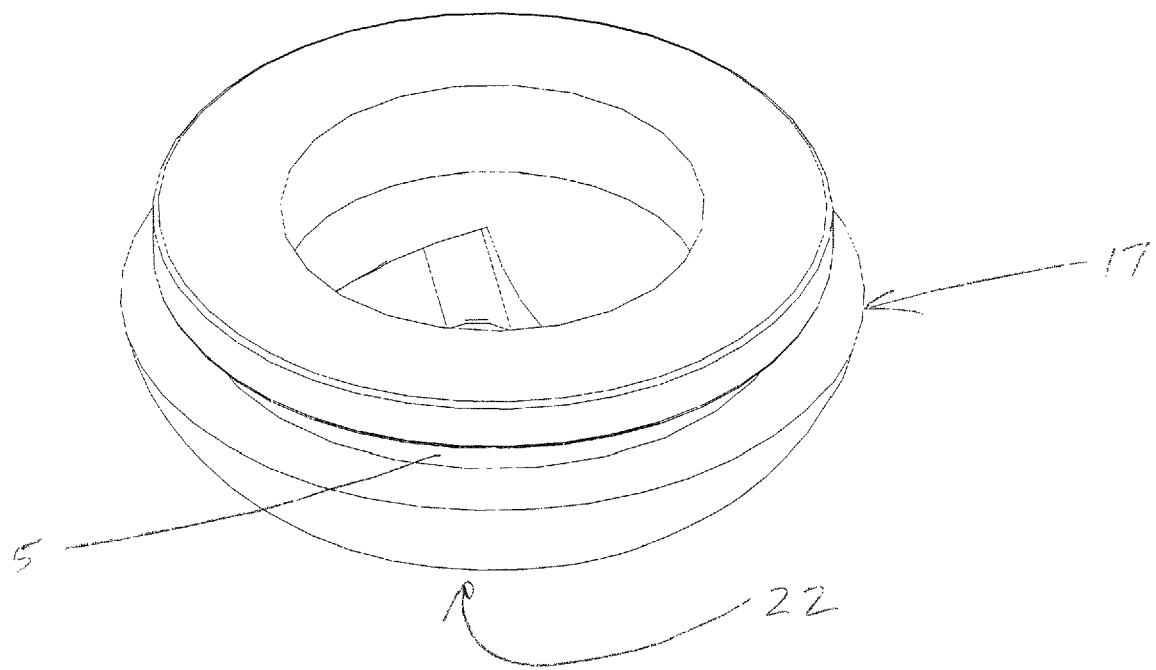
FIG. 4C is a side view of the lower portion of the housing shown in FIGS. 4A and 4B.
Figure 4D:
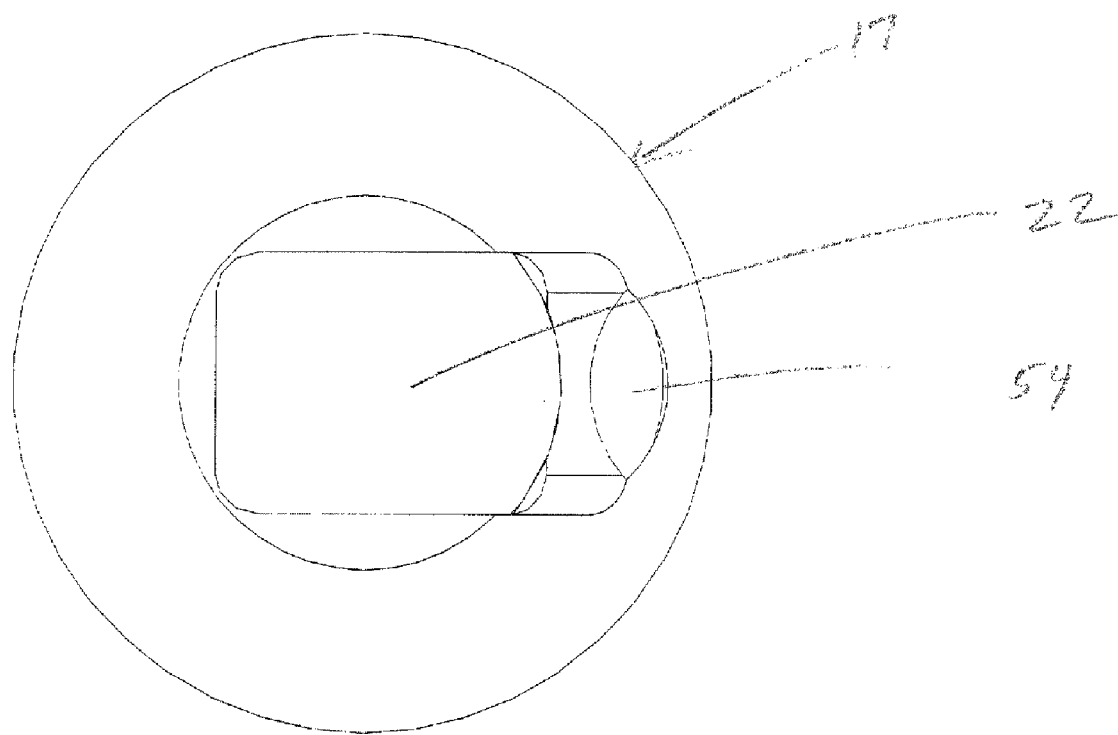
FIG. 4D is a lower view of the lower portion of the housing shown in FIGS. 4A and 4B.
Figure 4E:
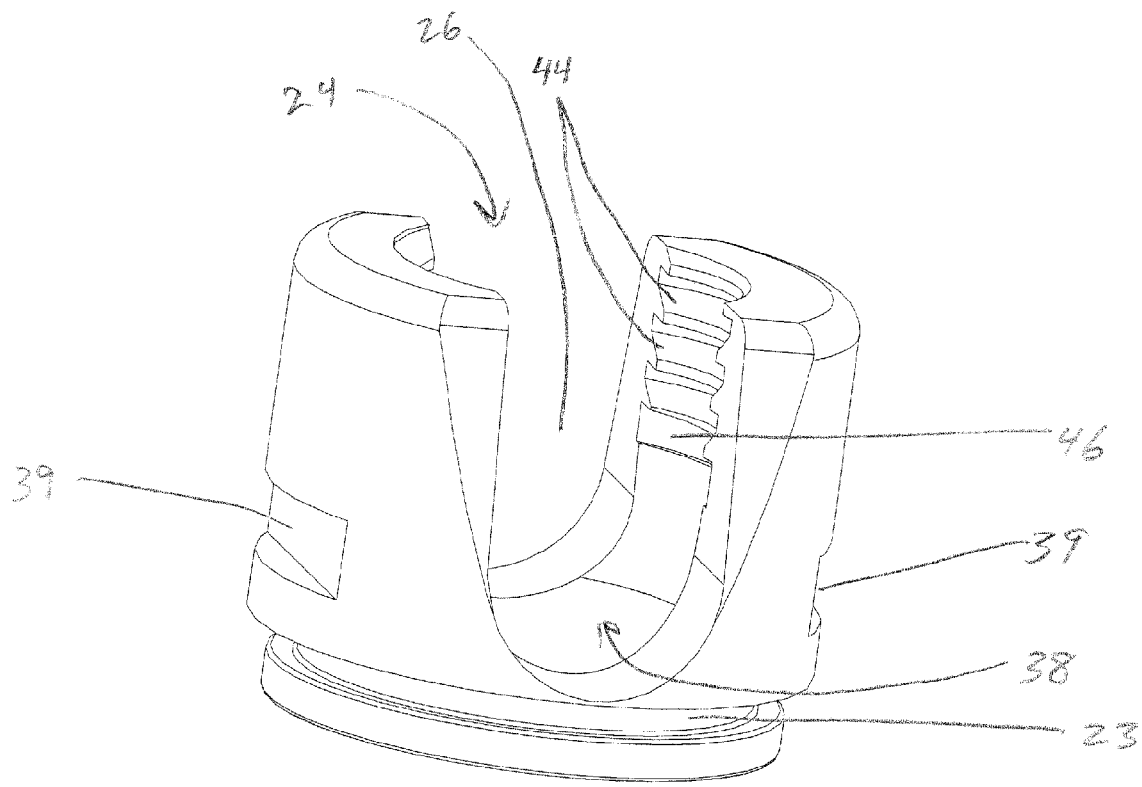
FIG. 4E is a side view of the upper portion of the housing shown in FIGS. 4A and 4B.

Proximal opening 22 may be circular or non-circular and may be centered on the central axis of housing 14 or biased to one side of the axis. For the sake of simplicity, non-circular dimensions of proximal opening 22 may be described relative to proximal opening being an oval, but it should be understood that other non-circular shapes may also be used without regard for the number or even the presence of an axis of symmetry. An oval has a major dimension, the largest distance between opposing sides of the oval, and a minor dimension, the smallest distance between opposing sides of the oval. When proximal opening 22 is non-circular, it has at least one dimension that is less than the diameter of head 30. It is not necessary for proximal opening 22 to have a lesser dimension than the diameter of head 30 in all directions, provided it has a lesser dimension in one direction. This permits head 30 to be retained securely in housing 14. Proximal opening 22 may further be biased in one direction relative to a central axis of housing 14 to permit a greater angle of attachment of bone screw 12 and therefore also, assembly 10 to a bone, regardless of whether it is circular or non-circular. One particular example is shown in FIG. 2, which provide a view of a generally ovoid proximal opening 22 as viewed upward from below housing 14 along the central axis of housing 14. An alternate example is provided in FIG. 3B, which provides a generally rectangular proximal opening 22 with rounded corners. As shown, proximal opening 22 may also have one or more chamfered edge 54.

As further described below, at least a portion of housing 14 may rotate or otherwise be adjustable to move the relative location of the bias of proximal opening 22 through 360 degrees around the axis of housing 14.

In one example, proximal opening 22 opens across an arc of between about 0 and about 80 degrees relative to the central axis of the housing. In another example, proximal opening 22 opens across an arc of between about 50 and about 70 degrees. However, in those embodiments where the location of proximal opening is adjustable, bone screw 12 can be oriented across a resulting conical angle that approaches a total of about 160 degrees due to the ability to adjust the location, and therefore the bias, of proximal opening 22 through 360 degrees around the central axis of housing 14. In comparison, when the opening is circular and centered, an opening of 50 degrees results in an included conical angle of 50 degrees. When the proximal opening is circular and biased by 25 degrees, an opening of 50 degrees results in a total available angulation of 100 degrees. This means the resulting angulation is not a true cone (i.e., a cone having a circular base), but a biased cone or a cone with an oval base when the opening is in a particular position relative to the central axis of the housing. However, rotation of the location of the biased proximal opening around the central axis of the housing results in an available angulation that can be represented as a true cone. For example, when the two part housing is used with a non-circular opening and the arc of the opening is 50 degrees, then the resulting available angulation is a full cone of as much as 100 degrees, with a circle as a base of the cone. Other possible non-circular shapes include a D-shaped opening.

Bone screw 12 is inserted into the interior cavity 26 of housing 14 and protrudes from proximal opening 22 for attachment to a bone such as a pedicle or other vertebral portion. Head 30 of bone screw 12 may have a slot 27 or other opening adapted to engage a screwdriver, hex driver or other similar driver for insertion of bone screw 12 into a bone.

Insert 16 may be described as being generally cylindrical, having a single central axis, with an outside diameter that corresponds to the inside diameter of housing 14 to allow insertion of insert 16 into cavity 26. Insert 16 is further configured such that it has a lower end 32 that is shaped to correspond to head 30 in such a way that lower end 32 engages head 30. For example, when head 30 is approximately spherical, lower end 32 is concave. Insert 16 additionally has a generally cylindrical channel 36 located approximately perpendicularly to the axis of the cylindrical shape of insert 16, creating an arcuate seat 34 in the walls of channel 36 for receiving a stabilizer such as a rod 18. In use, insert 16 is oriented such that channel 36 cooperates with channel 38 of housing 14 to permit alignment of rod 18 through both insert 16 and housing 14. Seat 34 may also have a slot 42 matching the configuration of slot 27 in head 30 of bone screw 12 to allow access to and manipulation of bone screw 12 through insert 16.

Channel 36 has a cross-sectional configuration that corresponds to the cross-sectional configuration of rod 18 such that arcuate seat 34 maintains contact with at least half of the portion of rod 18 that lies within channel 36, omitting from consideration the area of slot 42. In one embodiment, arcuate seat 34 maintains contact with more than half of the circumference of rod 18 that lies within channel 36. In another example, arcuate seat 34 maintains contact with about two thirds or more of the circumference of rod 18 that lies within channel 36. In this manner, any load to be transferred between rod 18 and seat 34 is distributed as evenly as possible across the length and width of seat 34. As a result of the presence of channel 36 in insert 16, the upper end of insert 16 includes two opposed tabs 40 located to each side of channel 36. Tabs 40 are configured in such a way that tabs 40 have a minor amount of flexibility, allowing them to flex outwardly within cavity 26 into inset areas 46 as rod 18 is inserted into and passes through channel 36 and is ultimately secured in seat 34. Flexibility of tabs 40 may be provided or at least supplemented by the presence of grooves 45 in the outer surface of insert 16. As rod 18 becomes seated into seat 34, tabs 40 will return to their original position interior to inset areas 46, securing rod 18 into place. In this way, a surgeon will have a tactile and/or audible response of a positive lock or "click" as tabs 40 return to their original position after rod 18 passes beyond tabs 40 in channel 36 and rod 18 becomes fully engaged in seat 34. The present invention also makes it unnecessary for there to be additional slits or other interruptions in the walls of insert 16 or housing 14 parallel to the central axis to allow for proper alignment of bone screw 12. In one particular embodiment, tabs 40 are devoid of any additional slits or other interruptions to maintain maximal contact between rod 18 and seat 34. Likewise, in another embodiment, the walls of housing 14 are devoid of slits or other interruptions other than channel 38. However, insert 16 may have grooves 45 of varying depths in the outer surface to control the flexibility of tabs 40 as described above. However, such grooves do not extend into channel 36.

Figure 6:
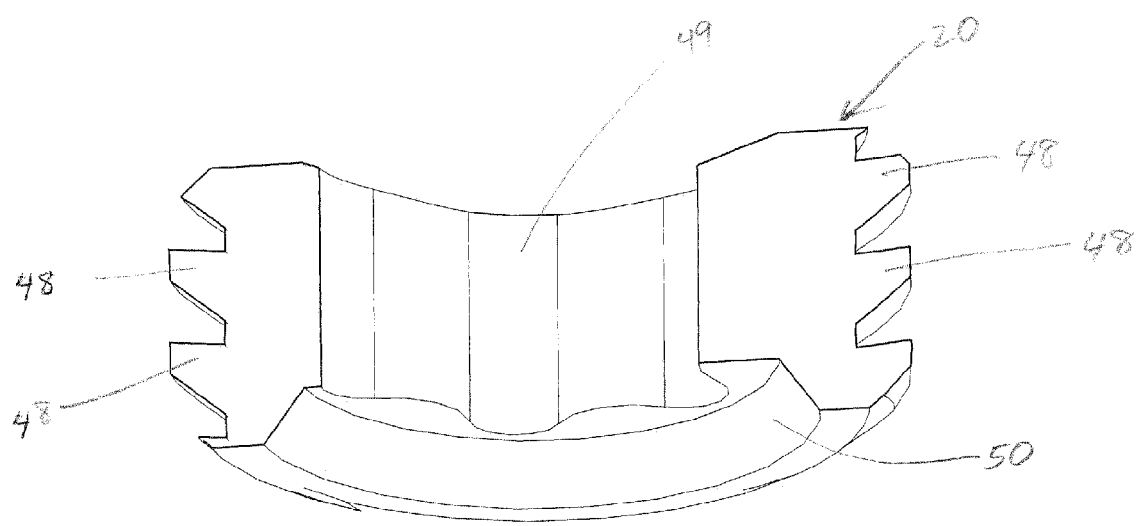
FIG. 6 is a cross sectional view of the set screw of the present invention.

Tabs 40 are further configured to have a chamfered top outer edge 43 to engage a set screw 20. Once rod 18 is fully engaged in seat 34, a set screw 20 is inserted into distal opening 24 of housing 14. As shown in FIG. 6, set screw 20 has outer threads 48 that engage threads 44 of housing 14 located in interior cavity 26. Set screw 20 may also have a slot 49 or other opening adapted to engaged a screwdriver, hexdriver or other similar driver for insertion of the set screw into housing 14. Set screw 20 further has an inwardly beveled bottom edge 50 that engages chamfered edge 43 of insert 16. As set screw 20 is secured in housing 14, bottom edge 50 of set screw 20 engages top edge 43 of insert 16 and prevents tabs 40 from flexing outward into inset areas 46, thereby locking tabs 40 into place and preventing movement of rod 18 within channel 36. In one embodiment, the engagement of set screw 20 and insert 16 results in the tabs 40 being locked in place and at least partially surrounding rod 18. Set screw 20 does not however, directly engage rod 18. Instead, pressure from set screw 20 is distributed to tabs 40 of insert 16 and locking pressure is exerted against a relatively large surface area of rod 18 by tabs 40. In this way, set screw 20 does not etch or otherwise deform or damage rod 18 and the possibility of damage to rod 18 during use is minimized. Additionally, the present design allows the bone screw assembly to dispense with external threads on housing 14 as well as a cap that utilizes such threads. In one particular embodiment, the outer surface of housing 14 is a smooth, uninterrupted surface, at least above grooves 39. Therefore, the present invention provides a bone screw assembly that is less bulky than prior designs.

The mechanism of rotation of a bias of proximal opening 22 may be achieved in any of several different ways. In the embodiments shown in FIGS. 3 and 4, housing 14 has an upper portion 15 and a lower portion 17. In FIG. 3, upper portion 15 has a series of detent locking members or clasps 51 located on the lower end of upper portion 15. Lower portion 17 similarly has a series of detent locking members or clasps 52 located on the upper end of lower portion 17. When lower portion 17 and upper portion 15 are engaged, clasps 51 and clasps 52 engage each other to provide an interference fit, locking upper portion 15 and lower portion 17 together but allowing rotation of upper portion 15 and lower portion 17 relative to each other. Lower portion 17 may be rotated into a predetermined orientation for proper positioning of proximal opening 22 relative to the upper portion of housing 14. In the example shown in FIG. 4, upper portion 15 and lower portion 17 may be clamped together by a pair of clamps 19. Clamps 19, for example, may be semicircular bands having a pair of ridges 21 running along upper and lower edges of the bands on the interior of the bands. These ridges 21 engage a groove 23 in upper portion 15 and a groove 25 in lower portion 17 of housing 14 with a interference fit, thereby locking upper portion 15 and lower portion 17 together while allowing lower portion 17 to be rotated to a predetermined orientation for proper positioning of proximal opening 22.

Figure 5:
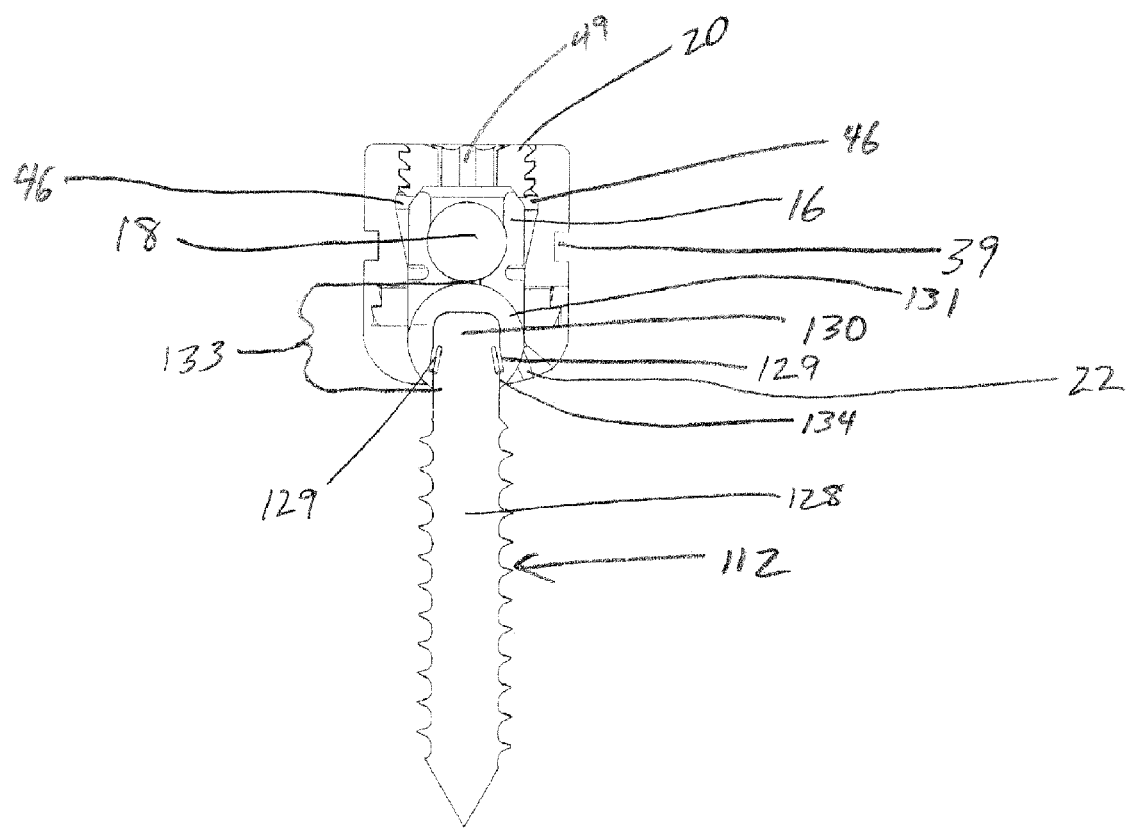
FIG. 5 is a cross sectional view of the embodiment shown in FIG. 3, as assembled.

The examples provided in FIGS. 3-5 also provide an additional advantage over prior bone screw designs, namely the ability to be used in minimally invasive surgery. A bone screw assembly 110 with an alternate bone screw design is illustrated. Bone screw 112 comprises a shaft 128 and a head 130. However, in this embodiment, head 130 itself is not spherical or even generally round in its overall configuration but may be described as approximately rectangular, narrowing curvedly to its point of attachment to shaft 128. Alternatively, head 130 can also be slightly inclined so that the side walls of the head flare outwardly slightly so as to create a subtle wedge configuration of at least a portion of head 130. Head 130 additionally has one or more tabs 129 projecting slightly from the surface of head 130. In the example shown, head 130 has a pair of tabs 129, each located on opposite sides of head 130 and projecting slightly from the surface of head 130. Bone screw assembly 110 also includes a bone screw clamp 131 which has a generally spherical outer surface with an interior channel 132. Interior channel 132 is configured to correspond to the shape of head 130, thereby allowing clamp 131 to be inserted over head 130 forming a generally spherical head assembly 133. Bone screw clamp 131 also has a pair of detent locking members 134 located adjacent to channel 132. When bone screw clamp 131 is placed on head 130, locking members 134 engage tabs 129, securing bone screw clamp 131 to head 130. Where head 130 has a wedge configuration as mentioned above, this configuration may also hinder removal of clamp 131 from head 130, providing additional strength to the fixation of clamp 131 to head 130.

In use, the bone screw design shown in FIGS. 3-5 permits the bone screw to be inserted into a bone without first being placed in housing 14 with shaft 128 protruding from housing 14, provided the dimensions of head portion 130 permit passage of head portion 130 through proximal opening 22. Instead, bone screw 112 may be inserted into a bone by itself using the relatively flat sides of head portion as attachment points for an insertion instrument (not shown). Once inserted into a bone, housing 14 may be placed on head portion 130 through proximal opening 22 and bone screw clamp 131 may then be secured onto head portion 130 using the locking interaction of detent locking member 134 with tabs 129 to prevent removal of bone screw clamp 131, thereby securing bone screw 112 within housing 14. In this way, bone screw 112 may be inserted as part of a minimally invasive surgical procedure, with the concomitant reductions in potential for surgical complications. As with the insert design described above, locking of detent locking members 134 with tabs 129 may give a surgeon a subtle tactile and/or audible response of the bone screw clamp 131 locking in place on the bone screw 112. Insert 16 and rod 18 are inserted into housing 14 as described above and set screw 20 is used to lock insert 16 and rod 18 in place as also described above.

Figure 7A:
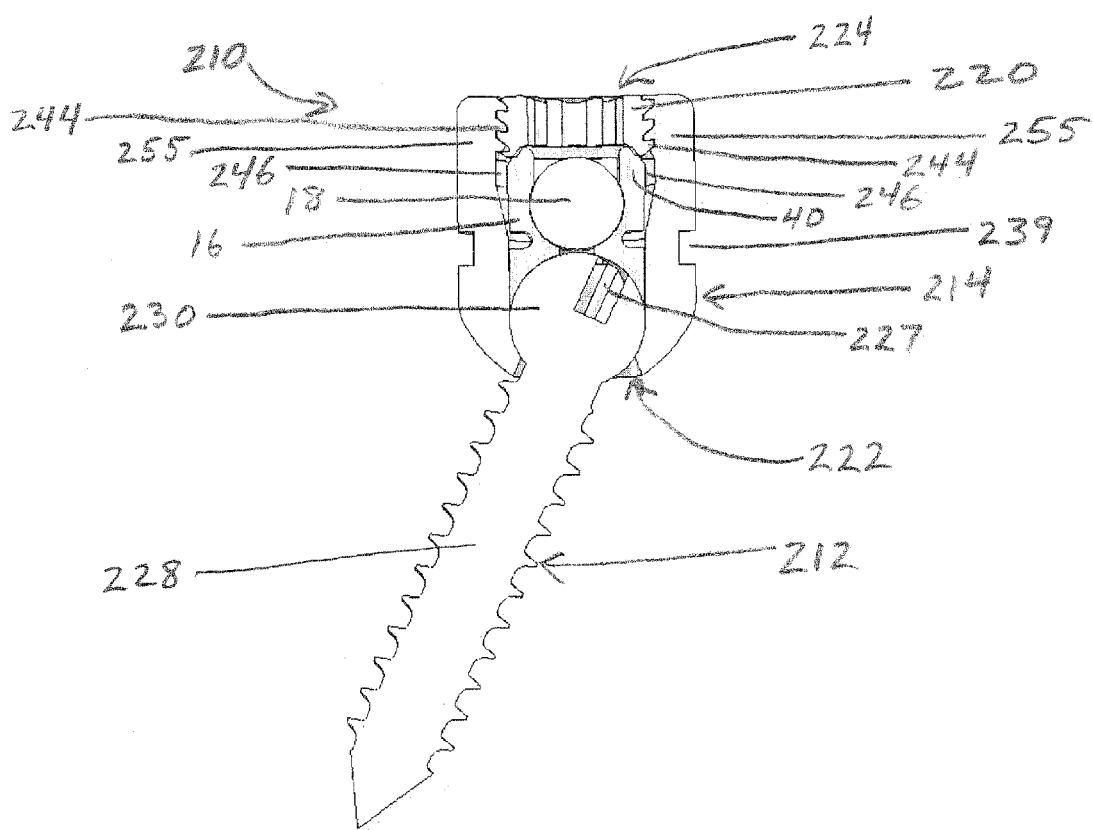
FIG. 7A is a cross sectional view of an embodiment of a bone screw assembly of the present invention.
Figure 7B:
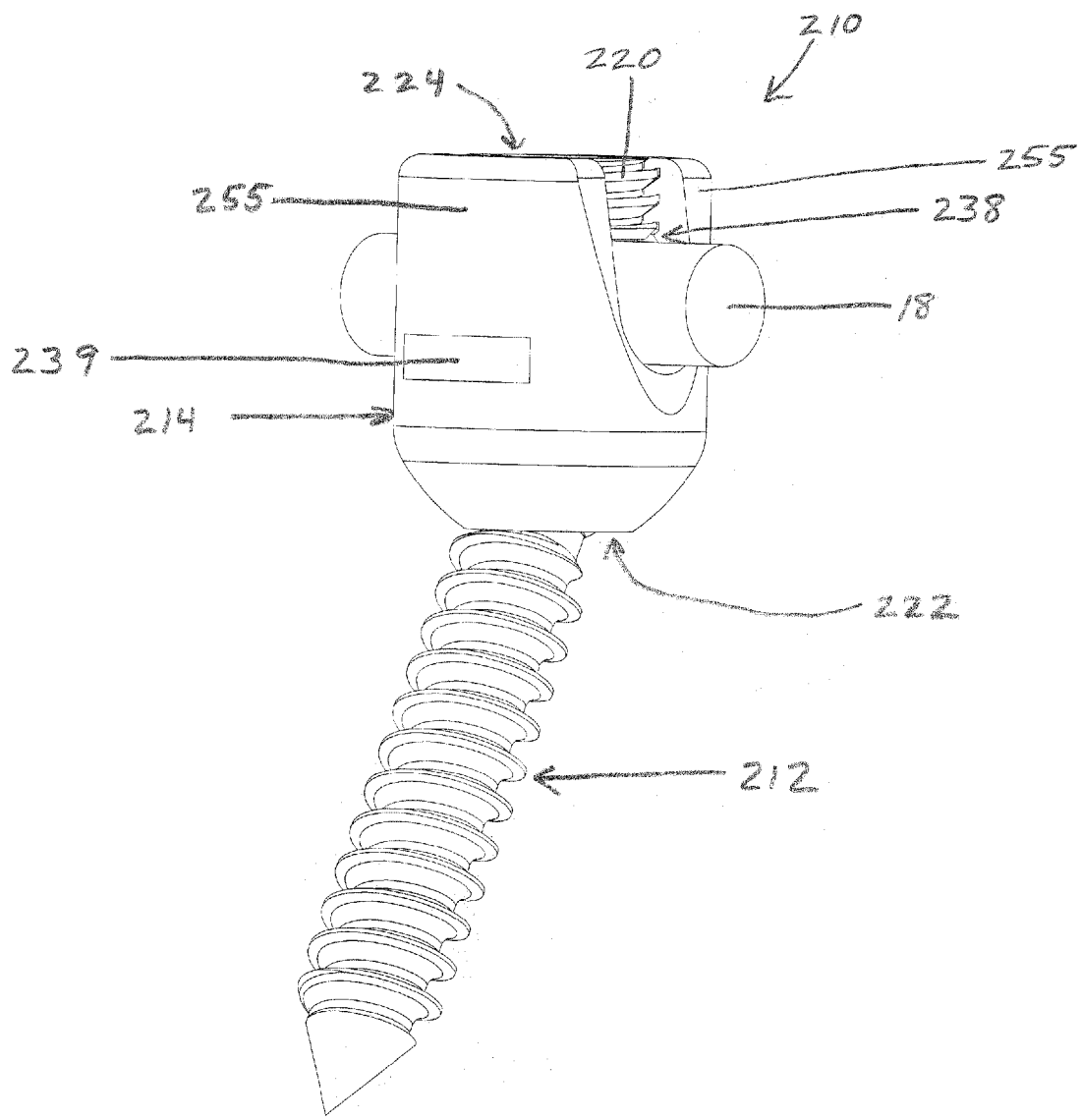
FIG. 7B is a side view of the bone screw assembly shown in FIG. 7A.
Figure 7C:
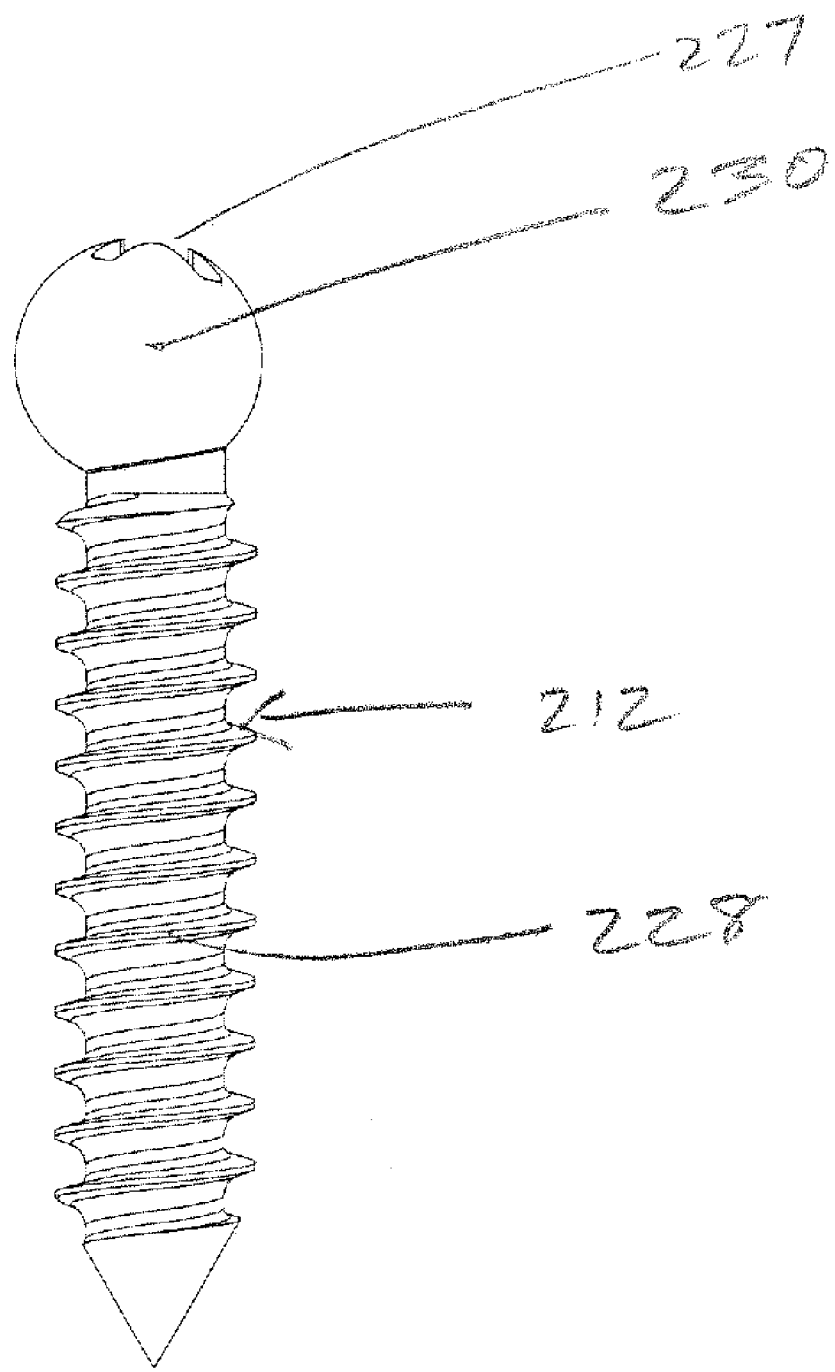
FIG. 7C is a side view of the bone screw shown in FIGS. 7A and 7B, shown in isolation.

In another embodiment, shown in FIGS. 7A-C, a bone screw assembly 210 comprises a bone screw 212 and a housing 214. Bone screw 212 has two portions, a shaft 228 and a head 230. In the examples shown, housing 214 is generally cylindrical with a single central axis and with a proximal opening 222 and a distal opening 224 accessing an interior cavity 226. Interior cavity 226 is generally cylindrical, along the central axis of housing 214. The lower end of cavity 226 adjacent to proximal opening 222 has an interior wall that narrows inwardly to generally accommodate the shape of head 230 when bone screw 212 is inserted through proximal opening 222. Housing 214 also has a channel 238, which is generally perpendicular to the axis of interior cavity 226. Channel 238 allows a stabilizer rod 18 or similar structure to be positioned within and extend through housing 214. The presence of channel 238 creates two opposed arcuate sections 255 in housing 214. The interior of sections 255 adjacent to distal opening 224 may be threaded with threads 244 to accommodate and engage set screw 220. Adjacent to threads 244 in cavity 226 are inset areas 246 which accommodate tabs 40 of insert 16, which may also be present as described above. Housing 214 may additionally have outer grooves 239 which provide a location for placement and grasping of the housing 214 by an insertion instrument (not shown). In one particular embodiment, the outer surface of housing 214 is devoid of threads on its upper end adjacent to distal opening 224 and presents a smooth, uninterrupted surface between grooves 239 and edge of the housing adjacent to distal opening 224.

Proximal opening 222 may be circular or non-circular and may be centered on the central axis of housing 14 or biased to one side of the axis. When proximal opening 222 is non-circular, it has at least one dimension that is less than the diameter of head 230. As with other embodiments described elsewhere herein, it is not necessary for proximal opening 222 to have a lesser dimension than the diameter of head 230 in all directions, provided it has a lesser dimension in one direction. This permits head 230 to be retained securely in housing 214. Proximal opening 222 may further be biased in one direction relative to a central axis of housing 214 to permit a greater angle of attachment of bone screw 212 and therefore also, assembly 210 to a bone, regardless of whether it is circular or non-circular.

In the example shown as bone screw assembly 210, the head 230 of bone screw 212 is not centered above shaft 228. That is, head 230 is biased to one side of the central axis of shaft 228. Bone screw 212 also has a slot 227 or opening adapted to engage a driver as previously described. Slot 227 is positioned generally at or near the center of a central axis of bone screw shaft 228. This results in slot 227 being offset relative to the top of head 230. In use, and particularly when used with a housing 214 with a proximal opening 222 that is biased to one side of the central axis of the housing 214, such a positioning of head 230 allows for a greater load to bear against the side of the housing compared to a traditional bone screw in which the head is centered on the central axis of the bone screw. In one embodiment, head 230 is biased between about 0.1 to about 3 mm from the central axis of shaft 228.

In still another embodiment, a bone screw assembly 310 comprises a bone screw 312, a housing 314 and a set screw 320. However, in the embodiment shown in FIGS. 8A-8D, there is no need for an insert 16 or similar structure, so the assembly 310 may be devoid of this additional part. In this embodiment, housing 314 is generally cylindrical with a single central axis, and with a proximal opening 322 and a distal opening 324 accessing an interior cavity 326. Interior cavity 326 is generally cylindrical following the central axis of housing 314. The lower end of cavity 326 adjacent to proximal opening 322 has an interior wall that narrows inwardly to generally accommodate the shape of head 330 when bone screw 312 is inserted through proximal opening 322. Housing 314 also has a channel 338, which is approximately perpendicular to the axis of interior cavity 326. Channel 338 allows a stabilizer rod 18 or similar structure to be positioned within and extend through housing 314. The presence of channel 338 creates two opposed arcuate sections 355 in housing 314. The interior of sections 355 adjacent to distal opening 324 may be threaded with threads 344 to accommodate and engage set screw 320. In this embodiment, housing 314 additionally comprises a pair of tabs 357 which extend essentially parallel to arcuate sections 355. Tabs 357 have an upper section 359 and a lower section 360. Upper sections 359 are approximately half the width of lower sections 360 and are configured to cooperate to essentially surround rod 18 in use. When a rod 18 is positioned in channel 338 and set screw 320 is engaged in housing 314 by threads 344, the rotational movement of set screw 320 will engage tabs 357 and deflect the tabs in such a way that at least the upper sections 359 of tabs 357 eventually surround rod 18. In the embodiment shown in FIG. 8B, each of tabs 357 is deflected by the clockwise motion of set screw 320 such that upper sections 359 eventually are positioned adjacent to each other, surrounding rod 18.

Additionally, a stabilizer base 361 may also be positioned within cavity 326 such that it forms the lower boundary of channel 338 and separates rod 18 from bone screw 312. Stabilizer base 361 may be shaped in a manner reminiscent of a springboard but with a concave upper surface to accommodate and secure rod 18 and to provide an additional arcuate contact between rod 18 and the remainder of assembly 310 rather than a simple point contact between rod 18 and bone screw 312. Stabilizer base 361 may be attached to housing 314 at one or more points.

Figure 8A:
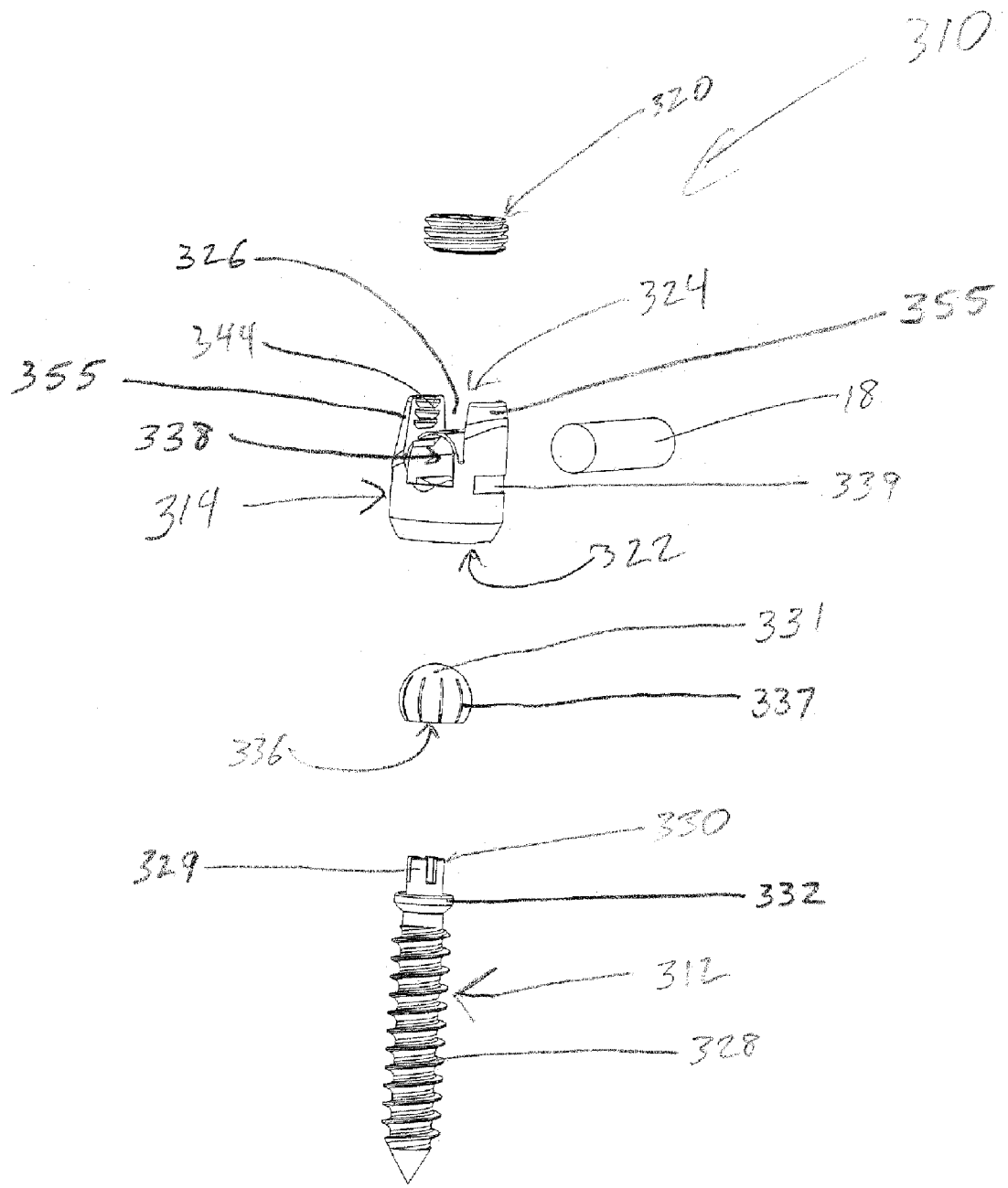
FIG. 8A is an exploded view of an embodiment of the bone screw assembly of the present invention.
Figure 8B:
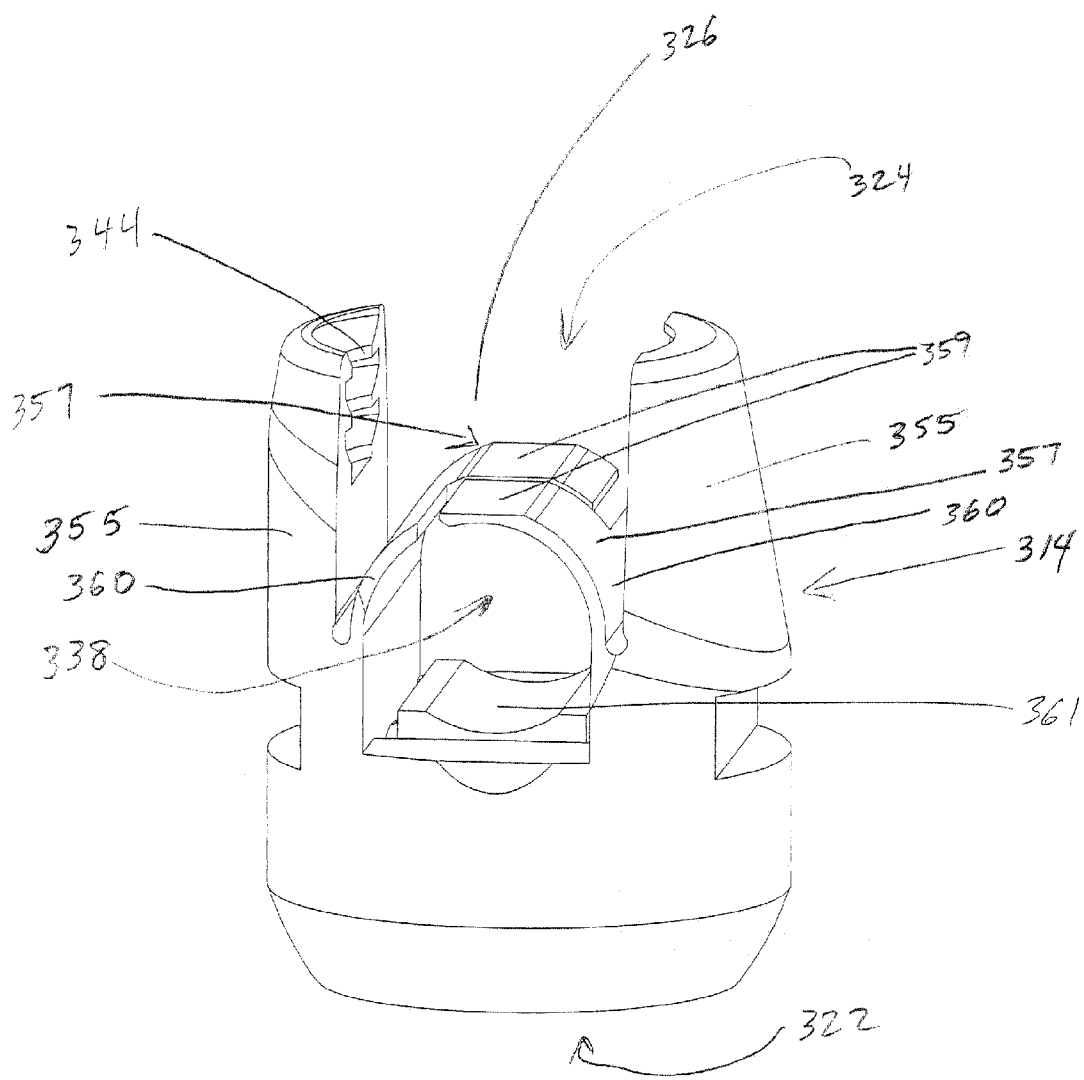
FIG. 8B is a side view of the housing shown in FIG. 8A.
Figure 8C:
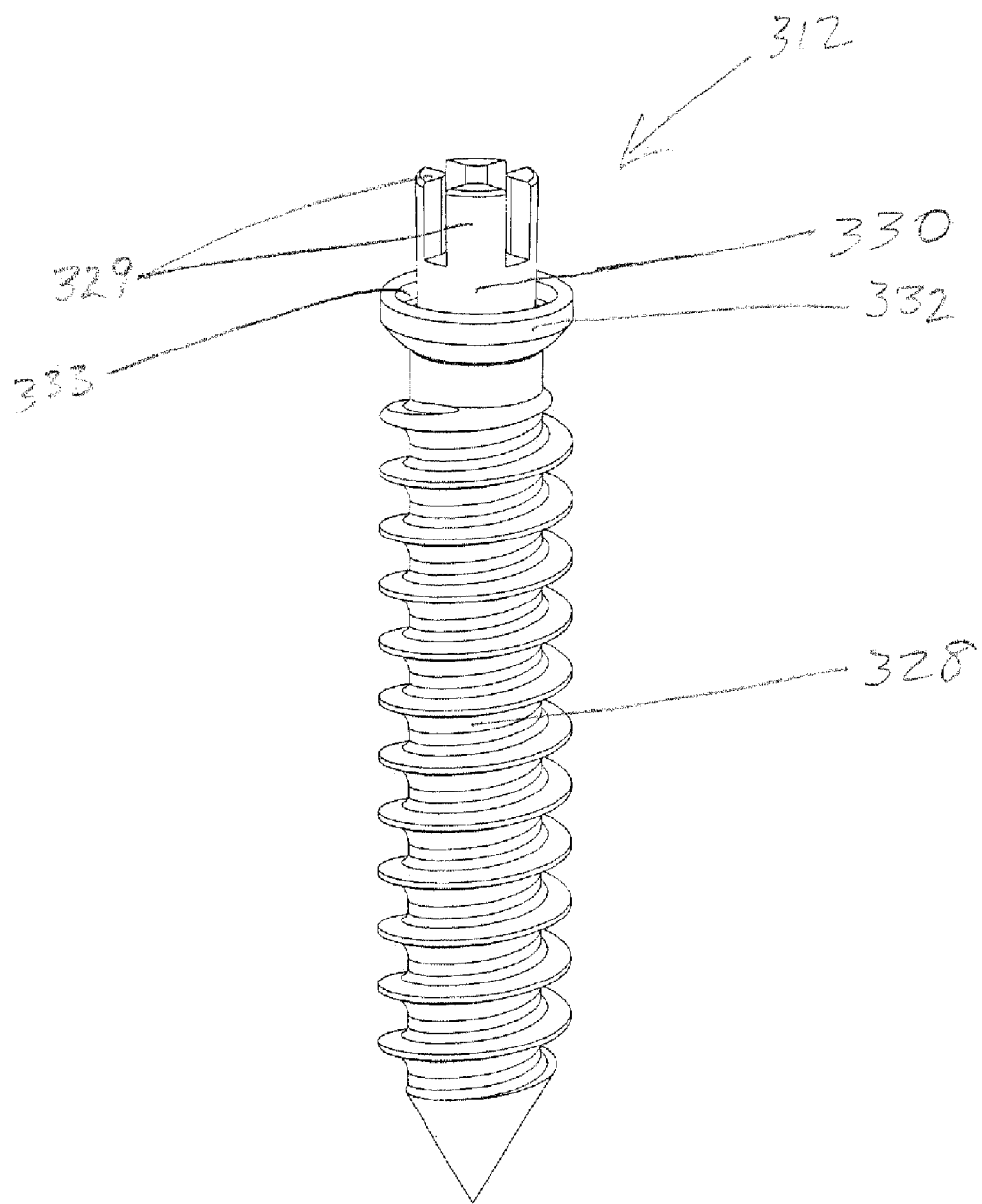
FIG. 8C is a side view of the bone screw shown in FIG. 8A.
Figure 8D:
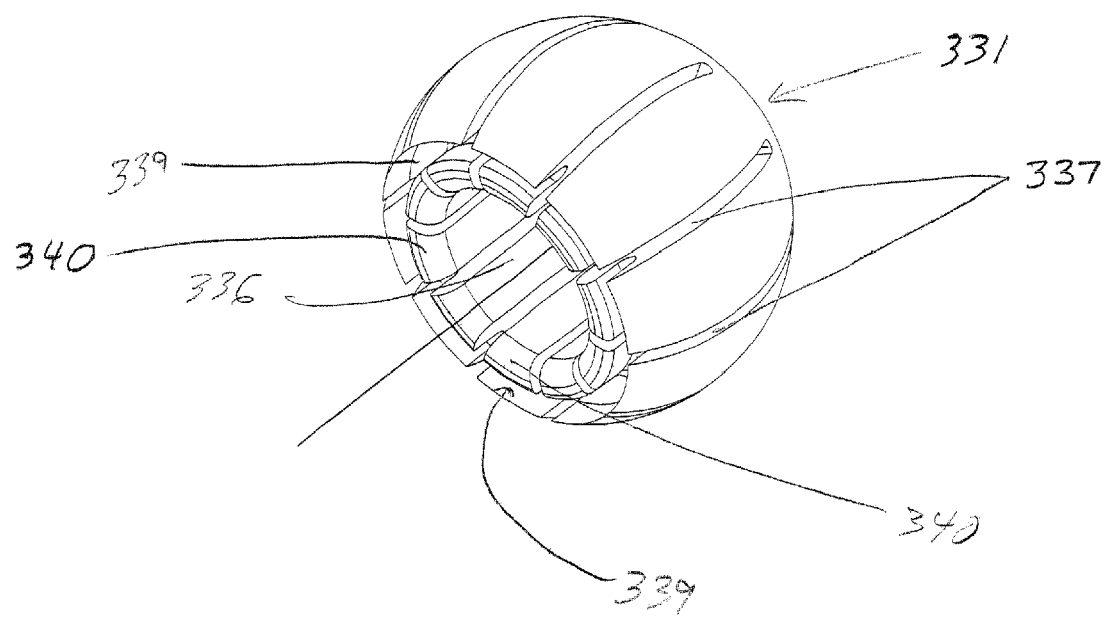
FIG. 8D is a perspective view of the bone screw cap shown in FIG. 8A.
Figure 9A:
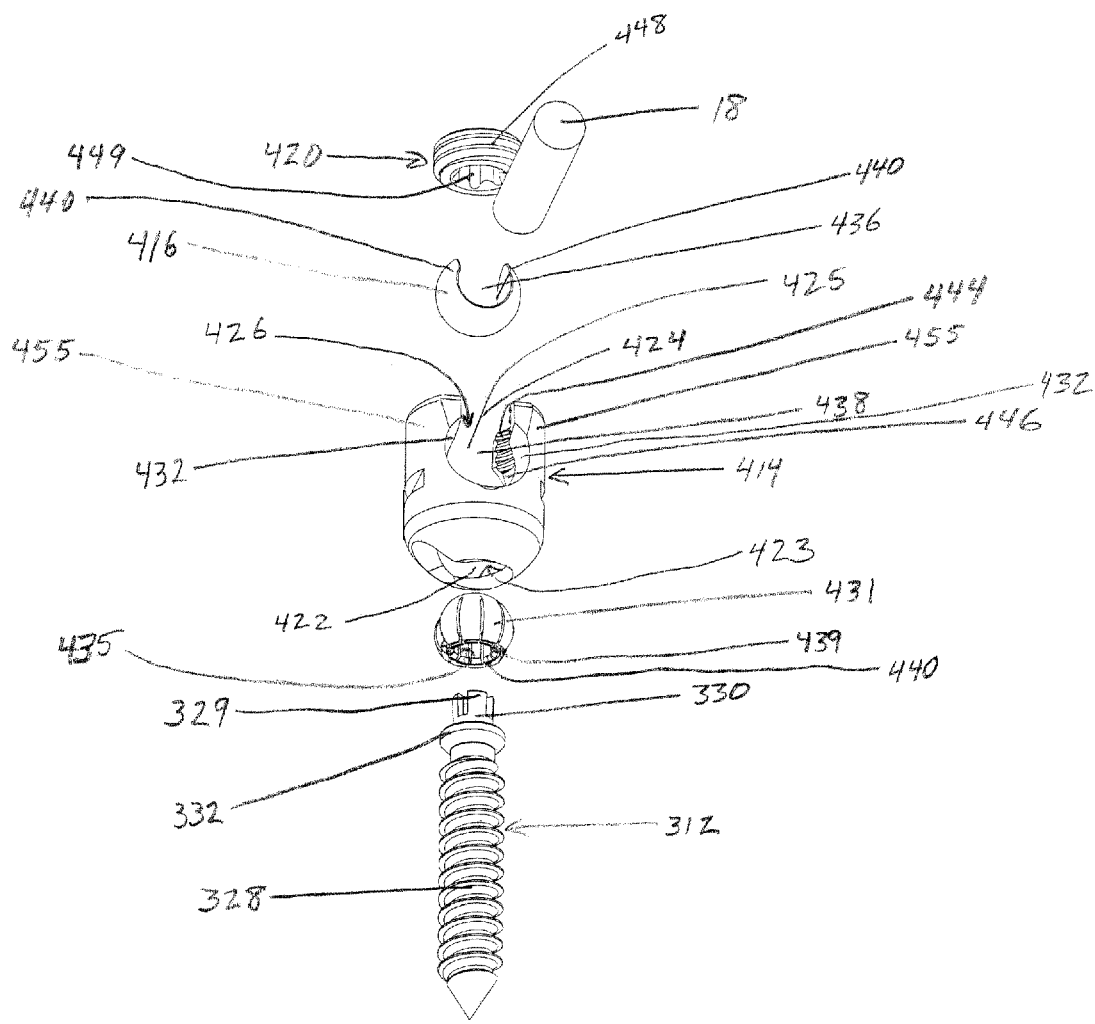
FIG. 9A is an exploded view of a bone screw assembly of the present invention.
Figure 9B:
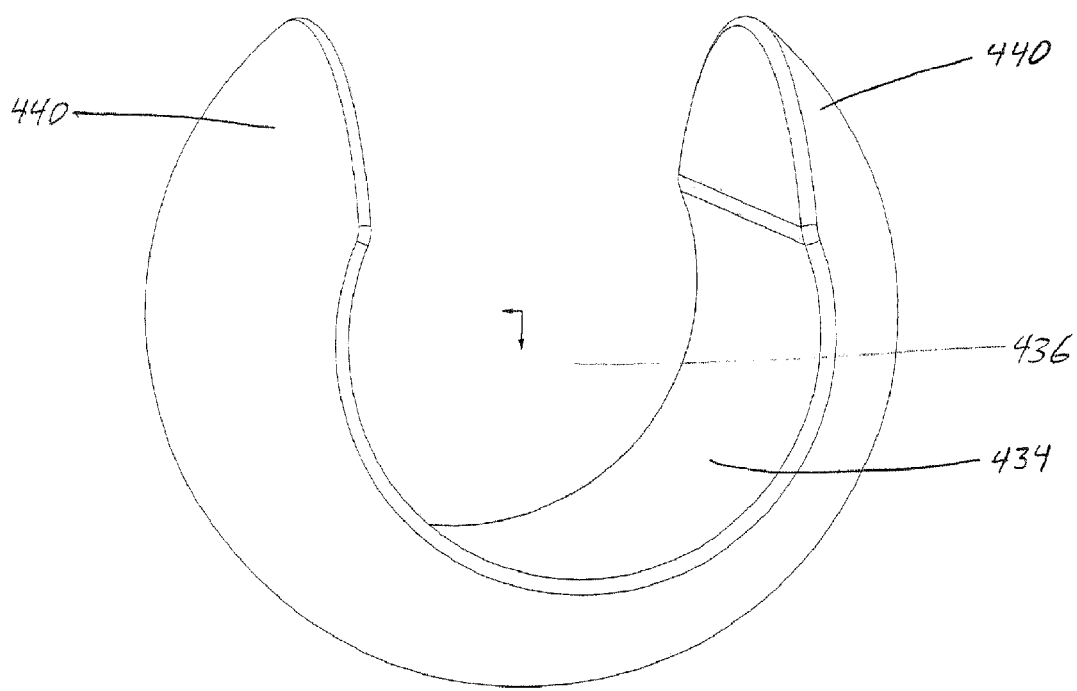
FIG. 9B is a side view of the retainer shown in FIG. 9A.
Figure 9C:
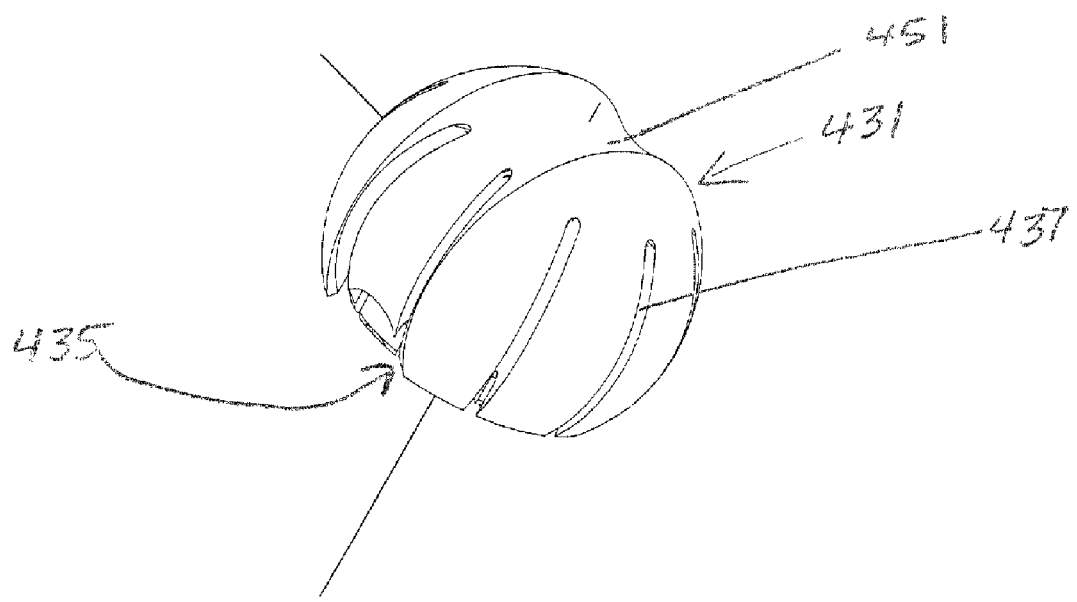
FIG. 9C is a perspective view of the bone screw cap shown in FIG. 9A.
Figure 9D:
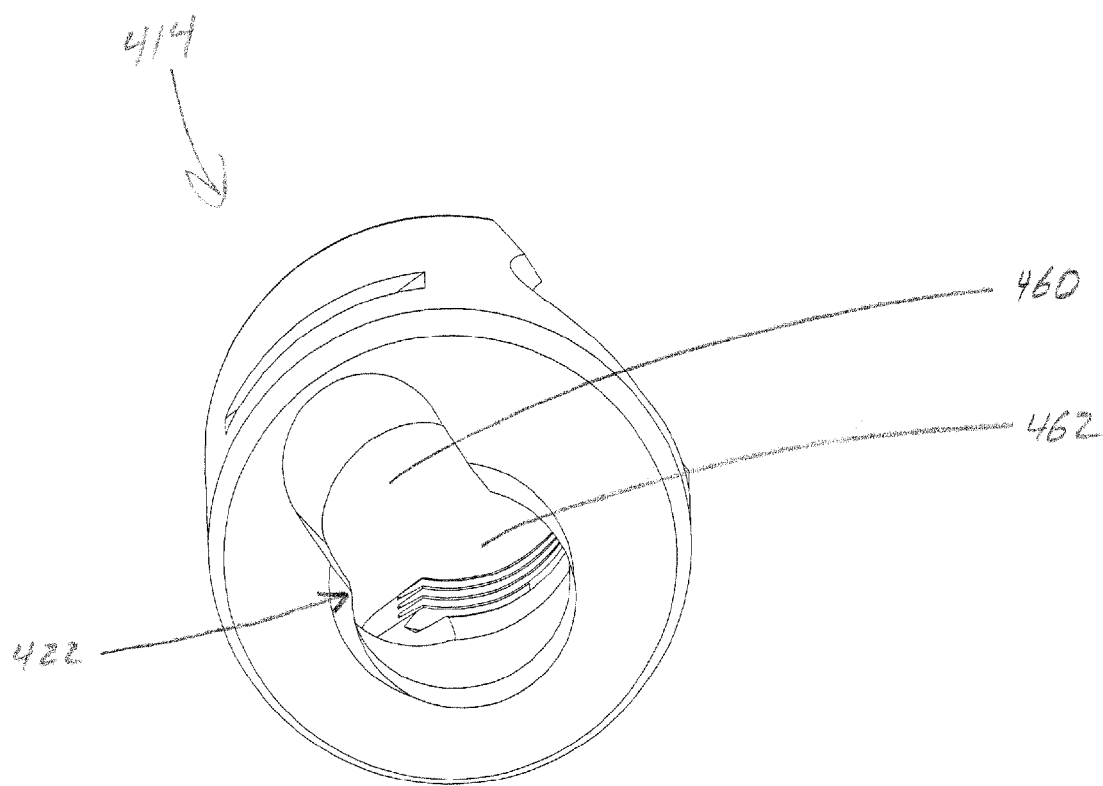
FIG. 9D is a perspective view of a housing of a bone screw shown in FIG. 9A.

In the embodiment shown in FIGS. 8A and 8C, bone screw 312 comprises a shaft 328 and a head 330. Head 330 as shown, is an essentially straight cylinder with one or more slots optionally cut into the head so as to permit engagement by a driver such as a screw driver and to form tabs 329. However, other configurations are also possible. For example, head 330 may have a tapered configuration where the diameter of head 330 reduces approaching shaft 328. Other geometries, tapered or untapered, may also be used such as those having an eliptical or polygonal cross section. Bone screw 312 also comprises a circumferential rim 332 adjacent to and extending outward from shaft 328 toward tabs 329 and forming an annular cavity 333 between rim 332 and head 330. Head 330 is adapted to receive a bone screw cap 331 which is adapted to fit onto and be received by tabs 329. To this end, cap 331 has an interior cavity 336 into which tabs 329 are received as shown in FIG. 8D. Cap 331 may have one or more slots 337 extending through the sides of cap 331 into cavity 336. Slots 338 permit minor amounts of deflection of the walls of cap 331 when tabs 329 are inserted into cavity 336, forming a friction or interference fit between cap 331 and head 330. Because slots 338 permit some deflection of the walls of cap 331, the diameter of cavity 336 may be the same as or slightly smaller that the diameter of head 330. Cap 331 also contains an annular cavity 339 which surrounds and is separated from interior cavity 336 by one or more tabs 340. Tabs 340 may be configured such that when cap 331 is inserted onto head 330, tabs 340 are engaged within annular cavity 333. Likewise, rim 332 is engaged within annular cavity 339. In the embodiment shown, cap 331 has a partial spherical shape, although other shapes are possible. When cap 331 engages on head 330, the slope of the sphere of cap 331 essentially matches the taper of rim 332 to provide an essentially uniform slope toward shaft 328.

In a further example, a bone screw assembly 410 comprises a bone screw 312, a housing 414 and a set screw 420. Housing 414 is generally cylindrical with a single central axis and with a proximal opening 422 and a distal opening 424 accessing an interior cavity 426. Interior cavity 426 comprises two generally spherical, connected cavities 423, 425 that connect to each other along the central axis of housing 414. The lower cavity 423 adjacent to proximal opening 422 has an interior wall that narrows inwardly to generally accommodate the shape of head 430 when capturing bone screw 412 and bone screw cap 431 inserted through proximal opening 422. The upper cavity 425 is also generally spherical to accommodate stabilizer retainer 416, which is inserted into cavity 425 through distal opening 424. Housing 414 also has a channel 438, which is approximately perpendicular to the axis of interior cavity 426. Channel 438 allows a stabilizer rod 18 or similar structure to be positioned within and extend through housing 414. The side walls of housing 414 bordering channel 438 may be chamfered to allow for angulation of rod 18 within channel 438. The chamfered areas 432 provide two axes of angulation of rod 18 on each side of housing 414, creating two conical areas of rod placement of up to 50 degrees in arc. The presence of channel 438 creates two opposed arcuate sections 455 in housing 414. The interior of sections 455 adjacent to distal opening 424 may have threads 444 to accommodate and engage set screw 420. Inset areas 446 are adjacent threads 444. In this embodiment, assembly 410 also comprises a stabilizer retainer 416 which is generally spherical in shape with a generally cylindrical channel 436 located therethrough creating an arcuate seat 434 in the walls of channel 436 for receiving a stabilizer such as a rod 18. In use, stabilizer retainer 416 is oriented such that channel 436 cooperates with channel 438 of housing 414 to permit alignment of rod 18 through both retainer 416 and housing 414.

Channel 436 has a cross-sectional configuration that corresponds to the cross-sectional configuration of rod 18 such that arcuate seat 434 maintains contact with at least half of the portion of rod 18 that lies within channel 436. In one embodiment, arcuate seat 434 maintains contact with more than half of the circumference of rod 18 that lies within channel 436. In another example, arcuate seat 434 maintains contact with about two thirds or more of the circumference of rod 18 that lies within channel 436. In this manner, any load to be transferred between rod 18 and seat 434 is distributed as evenly as possible across the length and width of seat 434. As a result of the presence of channel 436 in retainer 416, the upper end of retainer 416 includes two opposed tabs 440 located to each side of channel 436. Tabs 440 are configured in such a way that tabs 440 have a minor amount of flexibility, allowing them to flex outwardly within cavity 426 into inset areas 446 as rod 18 is inserted into and passes through channel 436 and is ultimately secured in seat 434.

Because retainer 416 is generally spherical, tabs 440 curve inwardly. Once rod 18 is fully engaged in seat 434, set screw 420 is inserted into distal opening 424 of housing 414. Set screw 420 has outer threads 448 that engage threads 444 of housing 414 located in interior cavity 426. Set screw 420 may also have a slot 449 or other opening adapted to engaged a screwdriver, hexdriver or other similar driver for insertion of the set screw into housing 414. Optionally, set screw 420 may further have an inwardly beveled bottom edge that engages curved tabs 440 of retainer 416 in a similar manner as a previously described embodiment. As set screw 420 is secured in housing 414, bottom edge 450 of set screw 420 engages tabs 440 and prevents tabs 440 from flexing outward into inset areas 446, thereby locking tabs 440 into place and preventing movement of rod 18 within channel 436. Alternatively, set screw 420 may be designed such that tabs 440 are positioned within a non-beveled bottom edge. As set screw 420 is secured in housing 414, the progression of set screw 420 locks tabs 440 in place and prevents them from flexing outwardly, thereby locking rod 18 in place in channel 436. The engagement of set screw 420 and retainer 416 results in the tabs 440 being locked in place and at least partially surrounding rod 18. Set screw 420 does not however, directly engage rod 18. Instead, pressure from set screw 420 is distributed to tabs 440 of retainer 416 and locking pressure is exerted against a relatively large surface area of rod 18 by tabs 440. In this way, set screw 420 does not etch or otherwise deform or damage rod 18 and the possibility of damage to rod 18 during use is minimized.

As with the previously described example, bone screw 312 comprises a shaft 328 and a head 330. Head 330 may be straight or a slightly outwardly tapered cylinder (with the diameter being larger at the top of the head than the diameter adjoining the rim 332) with one or more slots optionally cut into the head so as to permit engagement by a driver such as a screw driver, hexdriver or other driver to place the bone screw and to form tabs 329. Bone screw 312 also comprises a circumferential rim 332 adjacent to and extending outward from shaft 328 toward tabs 329 and forming an annular cavity 333 between rim 332 and head 330. Consistent with the previous example, head 330 is adapted to receive a bone screw cap 431 which is adapted to fit onto and be received by tabs 329 of head 330. Cap 431 has an interior cavity 435 into which tabs 329 of head 330 are received. Cap 431 may have one or more slots 437 extending though the sides of cap 431 into cavity 435. Slots 437 permit minor amounts of deflection of the walls of cap 431 when tabs 329 are inserted into cavity 435, particularly when head 330 is tapered as mentioned above, forming an interference fit between cap 431 and head 330. Cap 431 also contains an annular cavity 439 which surrounds and is separated from interior cavity 435 by tabs 440. Annular cavity 439 may also include a tapered diameter to match a tapered head 330, as mentioned above, due to the wedge-like configuration of head 330 in cavity 435, thereby increasing the resistance of separating cap 431 and head 330 when fully engaged. Tabs 440 may be configured such that when cap 431 is inserted onto head 330, tabs 440 are engaged within annular cavity 333. Likewise, rim 332 is engaged within annular cavity 439. This configuration provides that a side angle force against cap 431 is carried not just by one surface-to-surface contact, but by two. In the embodiment shown, cap 431 has a partial spherical exterior shape, although other shapes are possible. When cap 431 engages on head 330, the slope of the sphere of cap 431 essentially matches the taper of rim 332 to provide an essentially uniform slope toward shaft 328. In this example, cap 431 differs from the previous example in that cap 431 additionally has a concave groove 451 in its outer surface. In use, retainer 416 engages cap 431 at groove 451. The presence of concave groove 451 permits a greater contact surface between cap 431 and retainer 416 than a single point contact, thereby providing a greater distribution of load from one component to another. The presence of groove 451 also provides a restraint against rotation of the cap out of alignment with proximal opening 422, thereby facilitating insertion of bone screw 312 into cap 431.

Additionally, proximal opening 422 may include a first portion 460 with a dimension marginally larger than the diameter of the shank of the screw but smaller than the outside diameter of rim 332, and a second portion 462 in communication with the first portion. Second portion 462 is generally circular, centered about 1-5° C. from the central axis of housing opposite first portion 460. Second portion 462 has a diameter that is marginally larger than the outer diameter of rim 332. First portion 460 allows bone screw 312 to pivot inside proximal opening 422 in a single plane and rotate freely along its own axis. First portion 460 is biased to one side up to 60 degrees from the central axis of the housing. In use, second portion 462 is the insertion point for the bone screw into the cap. As soon as the bone screw pivots into 0 degrees of angulation, relative to the central housing axis (i.e. the bone screw is directly aligned with the central axis of the housing), direct contact occurs between bone screw and housing. Additionally, there is bone screw-housing contact as the bone screw pivots into first section 460. This provides a direct bone screw-to-housing contact surface, in contrast to other prior designs, which transfer a load from a bone screw to an insert to the housing, which can plastically deform the insert or pull it out. Alternatively, second portion 462 may be D-shaped (not shown) with the flat side of the "D" forming the boundary between first portion 460 and second portion 462, to enhance contact between the bone screw and housing at 0 degrees of angulation and into first portion 460.

Figure 10A:
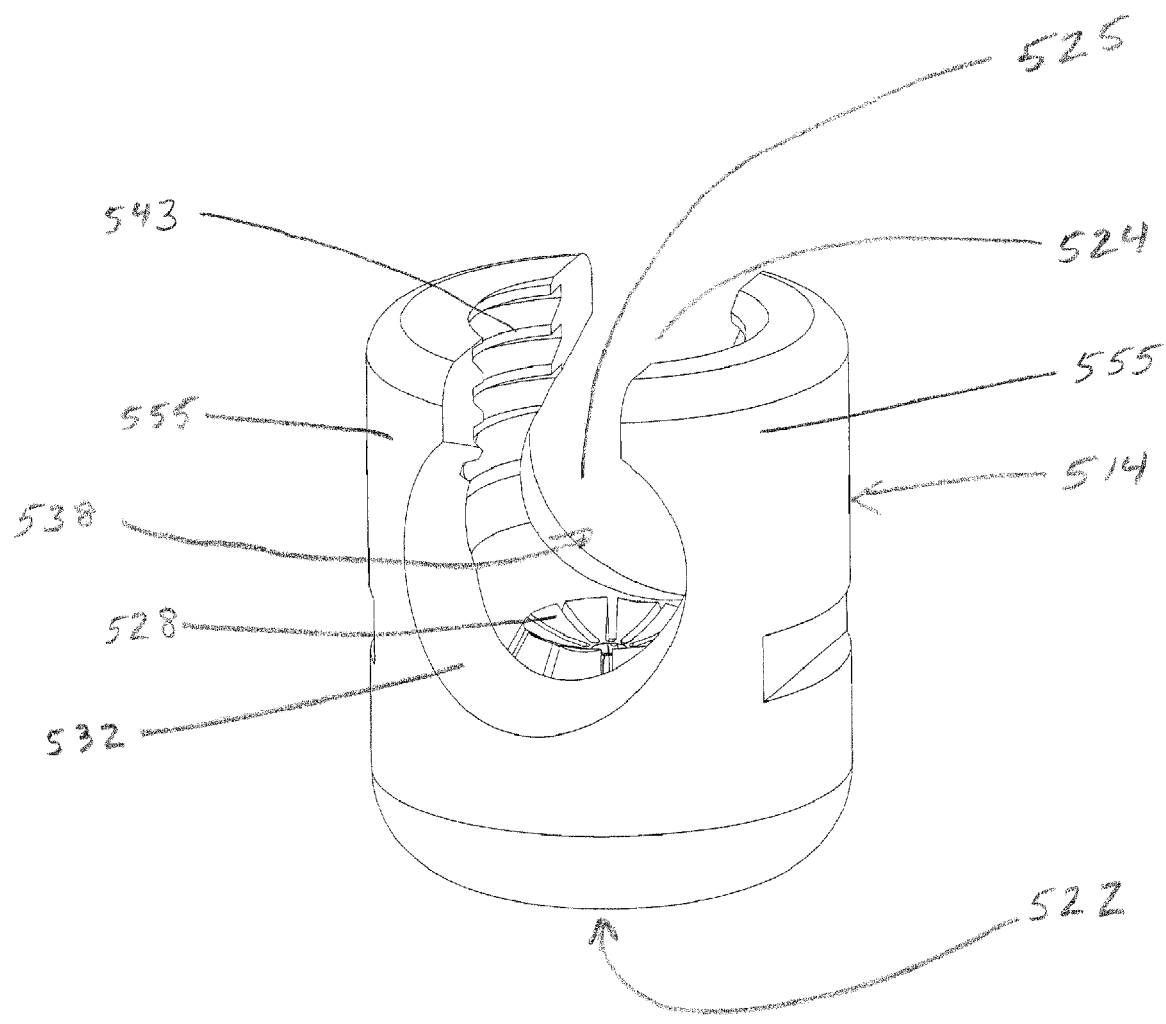
FIG. 10A is a perspective view of one example of a housing of a bone screw assembly of the present invention.
Figure 10B:
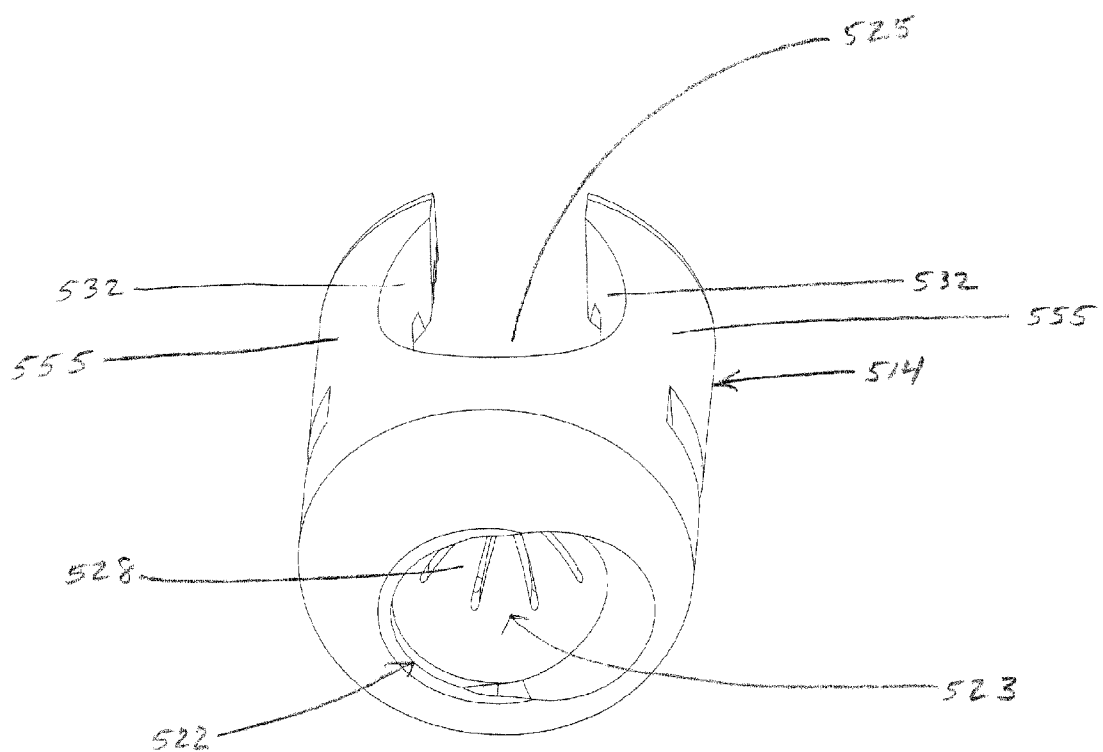
FIG. 10B is a perspective view of the example of a housing shown in FIG. 10A, from an alternate elevation.
Figure 10C:
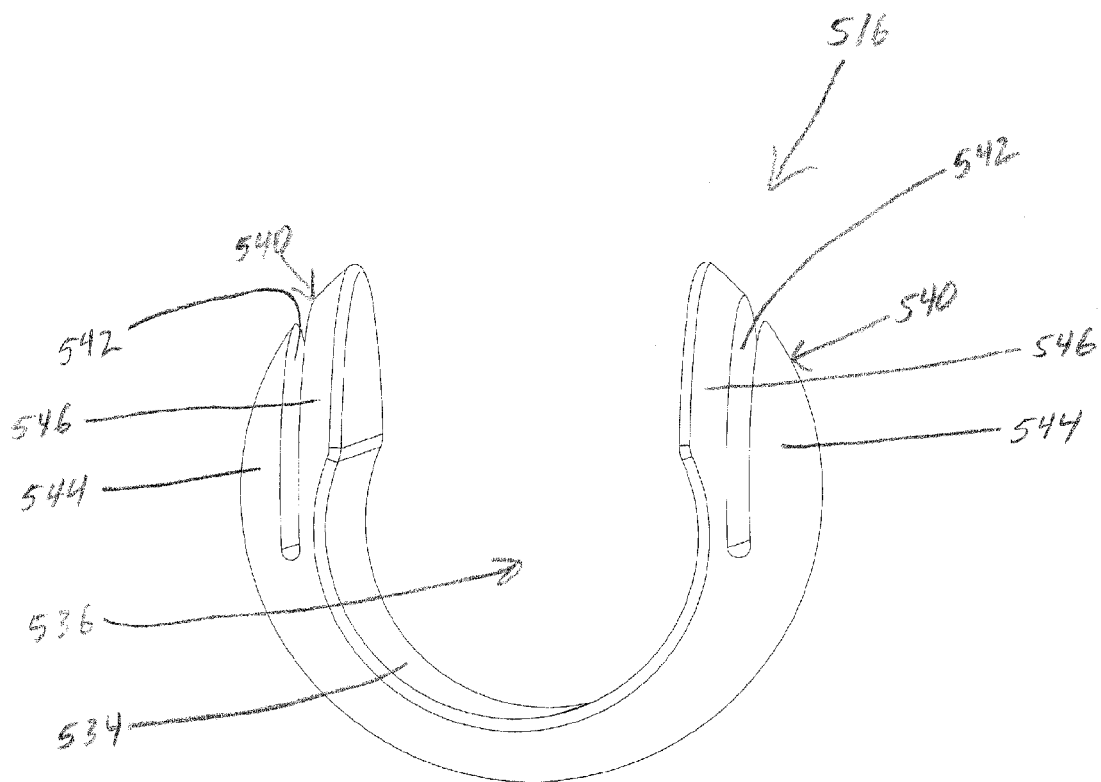
FIG. 10C is a side view of an alternate retainer from that shown in FIG. 9B.

Alternate configurations for the housing and the stabilizer retainer are shown in FIG. 10. Housing 514 is generally cylindrical with a single central axis and with a proximal opening 522 accessing a lower cavity 423 and a distal opening 524 accessing an upper cavity 526. Lower cavity 423 is at least partially spherical, while upper cavity 526 may be generally cylindrical or spherical. Upper cavity 526 and lower cavity 523 communicate through a diaphragm member 528 located therebetween upper cavity 526 and lower cavity 523. The lower cavity 423 has an interior wall that is adapted to generally accommodate the shape of head 330 when capturing bone screw 312 and bone screw cap 331 inserted through proximal opening 522. The upper cavity 525 is adapted to accommodate stabilizer retainer 516, which is inserted into cavity 525 through distal opening 424. Additionally, diaphragm member 528 may be curved, forming an arcuate seat in the base of upper cavity 525, or otherwise adapted to conform to the shape of stabilizer retainer 516 such that contact between stabilizer retainer 516 and diaphragm member 528 (and therefore housing 514) is greater than a single point contact. Housing 514 also has a channel 538, which is approximately perpendicular to the axis of housing 514. Channel 538 allows a stabilizer rod 18 or similar structure to be positioned within and extend through housing 514. The side walls of housing 514 bordering channel 538 may be chamfered to allow for angulation of rod 18 within channel 538 similar to previously described embodiments. The chamfered areas 532 provide two axes of angulation of rod 18 on each side of housing 514, creating two conical areas of rod placement of up to 50 degrees in arc. The presence of channel 538 creates two opposed arcuate sections 555 in housing 514. The interior of sections 555 adjacent to distal opening 524 may have threads 543 as in previously described embodiments.

In this embodiment, a stabilizer retainer 516 is generally spherical in shape with a generally cylindrical channel 536 located therethrough creating an arcuate seat 534 in the walls of channel 536 for receiving a stabilizer such as a rod 18. In use, stabilizer retainer 516 is oriented such that channel 536 cooperates with channel 538 of housing 514 to permit alignment of rod 18 through both retainer 516 and housing 514.

The presence of channel 536 creates a pair of opposed tabs 540 as in previously described embodiments. However, stabilizer retainer 516 differs from previous examples in that each tab 540 has a channel 542 separating a first outer tab portion 544 from a second inner tab portion 546. The presence of channels 542 permit inner tab portions 546 to engage a set screw inserted into distal opening 524 of housing 514. As a set screw is secured in housing 514, the bottom edge of the set screw engages inner tab portions 546 of tabs 440 and prevents inner tab portions 546 from flexing outward, thereby locking rod 18 within channel 536. However, the separation of inner tab portions 546 from outer tab portions 544 also permits rod 18 to be secured in such a way as to still allow the pivoting of rod 18, not only side-to-side (relative to the central axis of housing 514), but also up and down. Stated another way, if the central axis of housing 514 is considered the x axis, a central axis of channel 536 is considered the y axis, and an axis perpendicular to both the x and y axes is considered the z axis, the current embodiment permits rod 18 to pivot not only in the plane of the x axis (toward or away from the z axis), but also in the plane of the y axis, while still being fully secured within housing 514. In one embodiment, the set screw is engaged in housing 514 in such a way as to engage inner tab portions 546 but not outer tab portions 544, allowing outer tab portions 544 to secure retainer 516 within upper cavity 525. As with previous embodiments, the set screw does not directly engage rod 18, but pressure from the set screw is distributed to retainer 516 and locking pressure is exerted against a relatively large surface area of retainer 516, preventing etch or other deformation or damage to rod 18.

Based upon the foregoing disclosure, it should now be apparent that the bone screw assembly and bone screw of the present invention will carry out the objects set forth hereinabove. It is, therefore, to be understood that any variations evident fall within the scope of the claimed invention and thus, the selection of specific component elements can be determined without departing from the spirit of the invention herein disclosed and described.

I claim:

1. A bone screw assembly comprising:
   a bone screw having a shaft and a head;
   a stabilizer retainer adapted to engage the head of the bone screw, wherein the stabilizer retainer is generally cylindrical in shape with a cylindrical channel therein adapted to receive a stabilizer, wherein the stabilizer retainer has flexible portions that allow passage of the stabilizer into the channel and wherein an arcuate wall of the channel is adapted to maintain contact with at least a majority of the stabilizer located within the channel;
   a set screw adapted to contact the stabilizer retainer;
   a housing having a proximal opening and a distal opening that open on an interior cavity, wherein the housing is adapted to receive the bone screw, the stabilizer retainer and the set screw in the interior cavity, wherein the housing has a channel adapted to permit the passage of the stabilizer though the housing, and wherein the housing is adapted to secure the set screw in the distal opening; and wherein the proximal opening is biased relative to a central axis of the housing;
   wherein the set screw and stabilizer retainer are adapted to engage in such a way that movement of the flexible portions of the stabilizer retainer is prevented, thereby maintaining contact between the stabilizer and the wall of the stabilizer retainer channel such that movement of the stabilizer from the stabilizer retainer is prevented.

2. The bone screw assembly of claim 1, wherein the head of the bone screw comprises a head base, at least one tab located on a side of and projecting from the head base and a head clamp containing at least one detent locking member adapted to interact with the at least one tab to provide an interference fit between the head base and the head clamp.

3. A bone screw assembly comprising a bone screw containing a shaft, a head, a circumferential rim adjacent to and extending outward from the shaft forming a first annular cavity between the rim and the head, and additionally comprising a bone screw cap having a cap interior cavity, the bone screw cap being adapted to engage the head of the bone screw, wherein the bone screw cap comprises one or more slots extending though the sides of the cap into the cap interior cavity, and wherein the bone screw cap additionally comprises a second annular cavity which surrounds the cap interior cavity and is separated from the cap interior cavity by one or more tabs, wherein the one or more tabs are configured to engage the first annular cavity and the rim is adapted to engage the second annular cavity when the bone screw cap is inserted onto the bone screw head, and wherein the head is adapted to receive and secure a bone screw cap comprising a cap interior cavity.

4. The bone screw assembly of claim 3, wherein the head has a polygonal cross section.

5. The bone screw assembly of claim 3, additionally comprising a generally cylindrical housing with a single central axis and with a proximal opening and a distal opening accessing a housing interior cavity, wherein the housing interior cavity comprises two generally spherical, connected cavities that connect to each other along the central axis of housing, and wherein the housing also has a channel, which is approximately perpendicular to the central axis of the housing, and is adapted to permit a stabilizer to be positioned within and extend through the housing.

6. The bone screw assembly of claim 5, additionally comprising a stabilizer retainer which is generally spherical in shape with a generally cylindrical second channel located therethrough creating an arcuate seat in the walls of the second channel for receiving a stabilizer, wherein the stabilizer retainer is adapted to cooperate with the first channel of the housing to permit alignment of the stabilizer through both the retainer and the housing.

7. The bone screw assembly of claim 5, wherein the proximal opening includes a first portion with a dimension marginally larger than the diameter of the shaft of the bone screw but smaller than the outside diameter of the rim, and a second portion in communication with the first portion wherein the second portion is generally circular, centered 1-5° opposite the first portion relative to the central axis of housing and has a diameter that is marginally larger than the outer diameter of the rim.

8. The bone screw assembly of claim 7, wherein the first portion is biased to one side up to 60 degrees and wherein when the bone screw pivots past 0 degrees of angulation relative to central axis, direct contact occurs between the bone screw and the housing.

9. The bone screw assembly of claim 3, additionally comprising a generally cylindrical housing with a single central axis and with a proximal opening accessing a lower, at least partially spherical cavity adapted to accommodate the bone screw and the bone screw cap when the bone screw is inserted through the proximal opening, and a distal opening accessing an upper cavity, and wherein the upper cavity is adapted to accommodate a stabilizer retainer, which is adapted to be inserted into the upper cavity through the distal opening, and wherein the housing also has a first channel, which is approximately perpendicular to the central axis of the housing, and is adapted to permit a stabilizer to be positioned within and extend through the housing, wherein the side walls of the housing bordering the first channel are chamfered and wherein the upper cavity and the lower cavity communicate through a diaphragm member located between the upper cavity and the lower cavity.

10. The bone screw assembly of claim 9, additionally comprising a generally spherical stabilizer retainer with a generally cylindrical second channel located therethrough creating an arcuate seat in the walls of the second channel for receiving a stabilizer and creating a pair of opposed tabs, wherein each of the tabs has a channel separating a first outer tab portion from a second inner tab portion.

11. The bone screw assembly of claim 3, wherein the head tapers such that the diameter of the head reduces approaching the shaft.

12. A bone screw assembly comprising a bone screw comprising a shaft and a head permanently attached to the shaft, wherein the shaft is threaded and has a central axis and a circumference formed by a major diameter of the threads of the shaft, wherein the head is located above the shaft and overlaps a projection of a cylinder extending from the circumference of the shaft, and wherein the head is biased to one side of the central axis of the shaft, and additionally comprising a generally cylindrical housing, wherein the housing comprises a single central axis and with a proximal opening and a distal opening accessing an interior cavity, a housing channel generally perpendicular to the central axis adapted to receive a stabilizer and creating two opposed arcuate sections in the housing.

13. The bone screw assembly of claim 12, wherein the head is biased from the central axis of the shaft between about 0.1 and about 3 millimeters.

14. The bone screw assembly of claim 12, wherein the housing is further adapted to receive a set screw.

15. The bone screw assembly of claim 14, wherein the proximal opening is biased relative to the central axis of the housing.

16. A bone screw assembly comprising:
a bone screw having a shaft and a head;
a stabilizer retainer, wherein the stabilizer retainer is generally spherical in shape with a generally cylindrical channel therein adapted to receive a stabilizer, and wherein the stabilizer retainer has a gap in a side wall of the stabilizer retainer sufficient to allow a stabilizer to be inserted through the gap; and
a housing having a proximal opening and a distal opening that each open on an interior cavity, wherein the housing is adapted to receive the bone screw and the stabilizer retainer in the interior cavity, wherein the housing has a channel adapted to permit the passage of the stabilizer though the housing, and wherein the stabilizer retainer is adapted to be secured within the housing.

17. The bone screw assembly of claim 16, wherein the proximal opening is biased relative to a central axis of the housing.

18. The bone screw assembly of claim 17, wherein the proximal opening includes a first portion with a dimension marginally larger than the diameter of the shaft of the bone screw but smaller than the head of the bone screw, and a second portion in communication with the first portion wherein the second portion is centered 1-5° from the first portion relative to the central axis of housing and has a diameter that is marginally larger than the outer diameter of the rim.

19. The bone screw assembly of claim 17, wherein the proximal opening is biased to one side of the central axis of the housing up to 60 degrees.

20. The bone screw assembly of claim 16, wherein the stabilizer retainer has flexible portions that allow passage of the stabilizer into the channel of the stabilizer retainer.

21. The bone screw assembly of claim 20, wherein the stabilizer retainer is adapted to be secured in the housing such that movement of the flexible portions of the stabilizer retainer is prevented, thereby maintaining contact between the stabilizer and the wall of the stabilizer retainer channel such that movement of the stabilizer from the stabilizer retainer is prevented.

22. The bone screw assembly of claim 21, wherein the stabilizer retainer is secured in the housing by being contacted by a set screw.

* * * * *

UNITED STATES PATENT AND TRADEMARK OFFICE
CERTIFICATE OF CORRECTION

PATENT NO. : 8,167,910 B2  
APPLICATION NO. : 11/549800  
DATED : May 1, 2012  
INVENTOR(S) : Carl Michael Nilsson Page 1 of 1

It is certified that error appears in the above-identified patent and that said Letters Patent is hereby corrected as shown below:

Title Page, Item (57) Abstract, line 11, change "though" to --through--.

Claim 1, Column 15, line 18, change "though" to --through--.

Claim 16, Column 17, line 14, change "though" to --through--.

Signed and Sealed this
Third Day of July, 2012

David J. Kappos
*Director of the United States Patent and Trademark Office*